US009933425B2

(12) United States Patent
Slusarewicz et al.

(10) Patent No.: US 9,933,425 B2
(45) Date of Patent: Apr. 3, 2018

(54) METHOD FOR THE QUANTIFICATION OF PARASITE EGGS IN FECES

(71) Applicant: MEP Equine Solutions LLC, Lexington, KY (US)

(72) Inventors: Pawel Slusarewicz, Lexington, KY (US); Eric W. Hauck, Lexington, KY (US)

(73) Assignee: MEP Equine Solutions LLC, Lexington, KY (US)

( * ) Notice: Subject to any disclaimer, the term of this patent is extended or adjusted under 35 U.S.C. 154(b) by 0 days.

(21) Appl. No.: 14/561,780

(22) Filed: Dec. 5, 2014

(65) Prior Publication Data
US 2015/0293091 A1 Oct. 15, 2015

Related U.S. Application Data

(60) Provisional application No. 62/059,262, filed on Oct. 3, 2014, provisional application No. 61/977,754, filed on Apr. 10, 2014.

(51) Int. Cl.
G01N 33/569 (2006.01)
G01N 33/53 (2006.01)

(52) U.S. Cl.
CPC ... *G01N 33/56905* (2013.01); *G01N 33/5308* (2013.01); *G01N 2333/43526* (2013.01)

(58) Field of Classification Search
None
See application file for complete search history.

(56) References Cited

U.S. PATENT DOCUMENTS

| 5,004,699 A | 4/1991 | Winters |
| 5,914,239 A | 6/1999 | Laine |
| 5,997,847 A | 12/1999 | Spiesel |
| 6,121,420 A | 9/2000 | Laine |
| 6,251,390 B1 | 6/2001 | Harman et al. |
| 6,399,571 B1 | 6/2002 | Gray et al. |
| 6,440,388 B1 | 8/2002 | Burns et al. |
| 6,847,480 B2 * | 1/2005 | Steenblik ............ G02B 21/0008 359/368 |
| 8,321,154 B2 | 11/2012 | Adourian et al. |
| 2007/0099234 A1 * | 5/2007 | Zhang .................. G01N 33/543 435/7.1 |
| 2009/0074818 A1 * | 3/2009 | Kapel .................... A61K 35/62 424/265.1 |
| 2010/0124574 A1 | 5/2010 | Kapel et al. |
| 2011/0045514 A1 | 2/2011 | Muntendam et al. |
| 2013/0045217 A1 | 2/2013 | Laaksonen et al. |
| 2013/0216560 A1 | 8/2013 | Laaksonen et al. |

FOREIGN PATENT DOCUMENTS

| CN | 102073872 | 5/2011 |
| CN | 103268494 | 8/2013 |
| EP | 0256536 | 2/1988 |
| JP | 2012008042 | 1/2012 |
| WO | WO 86/00704 | 1/1986 |
| WO | WO 92/17786 | 10/1992 |
| WO | WO 99/46390 | 9/1999 |
| WO | WO 2005/005955 | 1/2005 |
| WO | WO 2011/161062 | 12/2011 |
| WO | WO 2013/068373 | 5/2013 |
| WO | WO 2013/068374 | 5/2013 |

OTHER PUBLICATIONS

Palmer et al. 1996 (Lectin Staining of Trichostrongylid Nematode Eggs of Sheep: Rapid Identification of Haemonchus contortus Eggs with Peanut Agglutinin; International Journal for Parasitology 26(40:447-450).*
Nelson et al. 2001 (Inactivation of Viable Ascaris Eggs by Reagants during Enumeration; Applied and Environmental Microbiology 67(12):5453-5459).*
Colditz et al. 2002 (Use of lectin binding characteristics to identify gastrointestinal parasite eggs in faeces; Veterinary Parasitology 105:219-227).*
International Preliminary Report on Patentability in International Application No. PCT/US2014/068860, dated Oct. 12, 2016, 13 pages.
'emdmillipore.com' [online]. "Immobilon Membranes, Sandwiched and Blotting Filter Paper," 2017, Retrieved from the internet: URL<http://www.emdmillipore.com/US/en/product/Immobilon-Membranes%2C-Sandwiches-and-Blotting-Filter-Paper,MM_NF-C3117> 3 pages.
International Search Report and Written Opinion in International Application No. PCT/US2014/068860, dated Feb. 18, 2015, 17 pages.
Ward et al., "Biology of Giardia Lamblia Detection of N-Acetyl-D-Glucosamine as the only surface saccharide moiety and identification of two distinct subsets of trophozoites by lectin binding," J Experimental Med., 1988, 167:73-88.
Zeiss Operating Manual Axiovert 200/200M, Mar. 30, 2001, Retrieved from the Internet: http://mcb.illinois.edu/microscopy/manuals/Axiovert200M_Manual.pdf [Retrieved on Jan. 27, 2015]; pp. 3-46.
Ajala and Asaolu, "Efficiency of the salt flotation technique in the recovery of Ascaris lumbricoides eggs from the soil," J Helminthol., Mar. 1995, 69(1):1-5.
Andersen et al., "SvSXP: a Strongylus vulgaris antigen with potential for prepatent diagnosis," Parasit Vectors, 2013, 6:84, 13 pages.
Arakane et al., "Properties of catalytic, linker and chitin-binding domains of insect chitinase," Insect Biochem. Mol. Biol., 2003, 33:631-648.
Bagley et al., Internal Parasites in Cattle. Beef Cattle Handbook. Iowa State University; 2014, 4 pages.
Brady and Nichols, "Drug resistance in equine parasites: an emerging global problem," J Equine Vet Sci., 2009, 29:285-295.

(Continued)

*Primary Examiner* — Mary Lyons
(74) *Attorney, Agent, or Firm* — Fish & Richardson P.C.

(57) ABSTRACT

Method and kits are provided determining the presence or absence of parasitic helminth eggs in environmental samples, particularly fecal samples. The methods incorporate egg capture methods and the use of N-acetyl-D-glucosamine specific ligands for egg detection.

20 Claims, 13 Drawing Sheets

(56) References Cited

OTHER PUBLICATIONS

Bueter et al., "Innate Sensing of Chitin and Chitosan," PLOS Pathogens, Jan. 2013, 9(1):e1003080, 3 pages.
Cernanska et al., "A survey on anthelmintic resistance in nematode parasites of sheep in the Slovak Republic," Vet. Parasitol., 2006, 135:39-45.
Cezar et al., "Multiple resistance of gastrointestinal nematodes to nine different drugs in a sheep flock in southern Brazil," Vet. Parasitol., 2010, 173:157-160.
Chan et al., "Adverse effect of the chitinolytic enzyme PjCHI-1 in transgenic tomato on egg mass production and embryonic development of Meloidogyne incognita," Plant Pathol., 2010, 59:922-930.
Chong et al., "Single-column purification of free recombinant proteins using a self-cleavable affinity tag derived from a protein splicing element," Gene, 1997, 192:271-281.
Chrispeels and Raikhel, "Lectins, Lectin Genes, and Their Role in Plant Defense," Plant Cell, Jan. 1991, 3:1-9.
Christie et al., "The sensitivity of direct faecal examination, direct faecal flotation, modified centrifugal faecal flotation and centrifugal sedimentation/flotation in the diagnosis of canine spirocercosis," J S Afr Vet Assoc., 2011, 82:71-75.
Chu et al., "A Bacillus amyloliquefaciens ChbB protein binds β- and α-chitin and has homologues in related strains," Microbiol., 2001, 147:1793-1803.
Colditz et al., 2002 "Use of lectin binding characteristics to identify gastrointestinal parasite eggs in faeces," Vet. Parasitol., May 2, 2002, 105(3):219-227.
Coles et al., "Anthelmintic resistance and use of anthelmintics in horses," Vet. Rec., 2003, 153:636.
Coles et al., "The detection of anthelmintic resistance in nematodes of veterinary importance," Vet. Parasitol., 2006, 136:167-185.
Cringoli et al., "The influence of flotation solution, sample dilution and the choice of McMaster slide area (volume) on the reliability of the McMaster technique in estimating the faecal egg counts of gastrointestinal strongyles and Dicrocoelium dendriticum in sheep," Vet Parasitol., 2004, 20:123:121-131.
Cringoli, "FLOTAC, a novel apparatus for a multivalent faecal egg count technique," Parassitologia, 2006, 48:381-384.
Crowe et al., "Monitoring of Human Immunodeficiency Virus Infection in Resource-Constrained Countries," Clinc Infectious Dis., 2003, 37(Suppl 1):525-35.
da Cruz et al., "Anthelmintic efficacy and management practices in sheep farms from the state of Rio de Janeiro, Brazil," Vet. Parasitol., 2010, 170:340-343.
Demain and Vaishnav, "Production of recombinant proteins by microbes and higher organisms," Biotechonol Advances, 2009, 27:297-306.
Demeler et al., "Discrimination of gastrointestinal nematode eggs from crude fecal egg preparations by inhibitor-resistant conventional and real-time PCR," PLoS. One., 2013, 8:e61285, 13 pages.
Duncan, "Internal parasites of the horse and their control," Equine Vet. J., 1985, 17:79-82.
Echeveria et al., "Evaluation of a blocking ELISA using a urease conjugate for the detection of antibodies to pseudorabies virus," J Vet Diagn Invest., 2000, 12:266-268.
Egwang and Slocombe, "Efficiency and sensitivity of techniques for recovering nematode eggs from bovine feces," Can J Comp Med., 1981, 45:243-248.
Egwang and Slocombe, "Evaluation of the Cornell-Wisconsin centrifugal flotation technique for recovering trichostrongylid eggs from bovine feces," Can J Comp Med., 1982, 46:133-137.
European Medicines Agency: Veterinary Medicines and Inspections, Committee for Veterinary Medical Products (CVMP), London, Jun. 26, 2006, 5 pages.
FDA, "Helpful Information for Veterinarians—Antiparasitic Resistance in Cattle and Small Ruminants in the United States: How to Detect it and What to Do About It," 2014, 5 pages.

Ferrari et al., "A fast, sensitive and easy colorimetric assay for chitinase and cellulase activity detection," Biotechnol Biofuels, 2014, 7:37, 8 pages.
Gao et al., "Characterisation and developmental expression of a chitinase gene in *Heterodera glycines*," Int. J.Parasitol., 2002, 32:1293-1300.
Gasbarre et al., "Further characterization of a cattle nematode population with demonstrated resistance to current anthelmintics," Vet. Parasitol., 2009, 166:275-280.
Goater et al., "Parasitism: The Diversity and Ecology of Animal Parasites," Second ed. Cambridge: Cambridge University Press, 2014, 514 pages.
Goldstein et al., "Characterization of the Cellulose-Binding Domain of the *Clostridium cellulovorans* Cellulose-Binding Protein A," J Bacteriology, Sep. 1993, 175(18):5762-5768.
Gordon and Martinez, "Alternative Activation of Macrophages: Mechanism and Functions," Immunity, May 2010, 32:593-604.
Gordon and Whitlock, "A new technique for counting nematode eggs in sheep faeces," J Counc Sci Ind Res., 1939, 12:50-52.
Greenwood et al., "Fusion to an endoglucanase allows alkaline phosphatase to bind to cellulose," FEB, Feb. 1989, 244(1):127-131.
Hardt and Laine, "Mutation of active site residues in the chitinbinding domain ChBD$_{ChiA1}$ from chitinase A1 of *Bacillus circulans* alters substrate specificity: use of a green fluorescent protein binding assay," Arch. Biochem. Biophys., 2004, 426:286-297.
Hashimoto et al., "Expression and characterization of the chitinbinding domain of chitinase A1 from Bacillus circulans WL-12," J. Bacteriol., 2000, 182:3045-3054.
Hatahet et al., "Disruption of reducing pathways is not essential for efficient disulfide bond formation in the cytoplasm of *E. coli*," Microbiol Cell Factories, 2010, 9:67, 9 pages.
Herasimenka et al., "A Selective Assay to Detect Chitin and Biologically Active Nano-Machineries for Chitin-Biosynthesis with Their Intrinsic Chitin-Synthase Molecules," Int J Mol Sci., 2010, 11:3122-3137.
Heuts et al., "Changing the substrate specificity of a chitooligosaccharide oxidase from *Fusarium graminearum* by model-inspired site-directed mutagenesis," FEBS Lett., 2007, 581:4905-4909.
Hillrichs et al., "Use of fluorescent lectin binding to distinguish *Teladorsagia circumcincta* and *Haemonchus contortus* eggs, third-stage larvae and adult worms," Parasitol Res., 2012, 110:449-458.
Hlatky et al., "Criteria for Evaluation of Novel Markers of Cardiovascular Risk: A Scientific Statement From the American Heart Association," Circulation, 2009, 119:2408-2416.
Hoglund et al., "A field survey on the status of internal parasites in calves on organic dairy farms in southwestern Sweden," Vet. Parasitol., 2001, 99:113-128.
Howell et al., "Prevalence of anthelmintic resistance on sheep and goat farms in the southeastern United States," J. Am. Vet. Med. Assoc., 2008, 233:1913-1919.
Hulett et al., "*Bacillus subtils* Alkaline Phosphatases III and IV," J Biol Chem., 1991, 266(2):1077-1084.
Hultgren et al., "Optimization of Yield in Magnetic Cell Separations Using Nickel Nanowires of Different Lengths," Biotechnol Progress, 2005, 21(2):509-515.
Ikegami et al., "Solution Structure of the Chitin-binding Domain of *Bacillus circulans* WL-12 Chitinase A1," J Biological Chem., 2000, 275(18):13654-13661.
Jackson and Coop, "The development of anthelmintic resistance in sheep nematodes," Parasitology, 2000, 120 Suppl, S95-107.
Jackson et al., "Anthelmintic resistance and management of nematode parasites on beef cattle-rearing farms in the North Island of New Zealand," N. Z. Vet. J., 2006, 54:289-296.
James et al., "Drug resistance mechanisms in helminths: is it survival of the fittest?" Trends Parasitol., 2009, 25:328-335.
Kania and Reinemeyer, "Anoplocephala perfoliata coproantigen detection: a preliminary study," Vet Parasitol., 2005, 127:115-119.
Kaplan, "Drug resistance in nematodes of veterinary importance: a status report," Trends Parasitol., 2004, 20:477-481.
Khan et al., "Double-Hexahistidine Tag with High-Affinity Binding for Protein Immobilization, Purification, and Detection on Ni-Nitrilotriacetic Acid Surfaces," Analytical Chem., 2006, 8 pages.

(56) References Cited

OTHER PUBLICATIONS

Koksharov et al., "*Bacillus subtilis* alkaline phosphatase IV acquires activity only late at the stationary phase when produced in *Escherichia coli*. Overexpression and characterization of the recombinant enzyme," Protein Expression Purification, 2013, 90:186-194.
Koksharov et al., Supplementary Material: *Bacillus subtilis* alkaline phosphatase IV acquires activity only late at the stationary phase when produced in *Escherichia coli*. Overexpression and characterization of the recombinant enzyme, Protein Expression Purification, 2013, 5 pages.
Kolbe et al., "The Streptomyces reticuli α-chitin-binding protein CHB2 and its gene," Microbiology, 1998, 144(Pt 5):1291-1297.
Kornele et al., "Antiparasitic resistance and grazing livestock in the United States," JAVMA, 2014, 244(9): 1020-1022.
Kunert, "On the mechanism of penetration of ovicidal fungi through egg-shells of parasitic nematodes. Decomposition of chitinous and ascaroside layers," Folia Parasitologica, 1992, 39:61-66.
Learmount et al., "Development and validation of real-time PCR 10 methods for diagnosis of Teladorsagia circumcincta and Haemonchus contortus in sheep," Vet. Parasitol., 2009, 166:268-274.
Lester et al., "A cost comparison of faecal egg countdirected Anthelmintic delivery versus interval programme treatments in horses," Vet Record, Oct. 2013, 4 pages.
Levecke et al., "The bias, accuracy and precision of faecal egg count reduction test results in cattle using McMaster, Cornell-Wisconsin and FLOTAC egg counting methods," Vet Parasitol., 2012, 188:194-199.
Lewis et al., "The different effector function capabilities of the seven equine IgG subclasses have implications for vaccine strategies," Mol Immunol., Feb. 2008, 45(3):818-827.
Linder et al., "Use of Recombinant Cellulose-Binding Domains of *Trichoderma reesei* Cellulase as a Selective Immunocytochemical Marker for Cellulose in Protozoa," Applied Environ Microbiol., May 2002, 68(5):2503-2508.
Molano et al., "Distribution of Chitin in the yeast cell wall: An Ultrastructural and Chemical Study," J Cell Biol., 1980, 85:199-212.
Montgomery et al., "A simple assay for chitin: application to sediment trap samples from the subarctic Pacific," Mar. Ecol. Prog. Ser., 1990, 64:301-308.
Nansen and Roepstorff, "Parasitic helminths of the pig: factors influencing transmission and infection levels," Int J Parasitol. Jun. 1999;29(6):877-91.
Nejadmoghaddam et al., "Profiling and quantitative evaluation of three Nickel-Coated magnetic matrices for purification of recombinant proteins: lelpful hints for the optimized nanomagnetisable matrix preparation," J Nanobiotechnol., 2011, 9:31, 11 pages.
Nicholls and Obendorf, "Application of a composite faecal egg count procedure in diagnostic parasitology," Vet Parasitol., 1994, 52:337-342.
Nielsen et al., "AAEP Parasite Control Guidelines," 2013. American Association of Equine Practioners, 24 pages.
Nielsen et al., "Analysis of multiyear studies in horses in Kentucky to ascertain whether counts of eggs and larvae per gram of feces are reliable indicators of numbers of strongyles and ascarids present," Vet. Parasitol., 2010, 174:77-84.
Nielsen et al., "Development of Strongylus vulgaris-specific serum antibodies in naturally infected foals," Vet Parasitol., 2014, 200:265-270.
Oguri, "Analysis of sugar chain-binding specificity of tomato lectin using lectin blot: recognition of high mannose-type N-glycans produced by plants and yeast," Glycoconjugate J., 2005, 22:453-461.
Olson et al., "Hierarchical assembly of the eggshell and permeability barrier in *C. elegans*," J Cell Biol., 2012, 198(4):731-748.
Palmer and McCombe, "Lectin staining of trichostrongylid nematode eggs of sheep: rapid identification of Haemonchus contortus eggs with peanut agglutinin," Int. J. Parasitol., 1996, 26:447-450.
Peregrine et al., "Anthelmintic resistance in important parasites of horses: does it really matter?" Vet. Parasitol., 2014, 201:1-8.
Peimin et al., "Prevalence of gastrointestinal helminths in different poultry production systems," Br. Poult. Sci., 1999, 40:439-443.
Perry and Randolph, "Improving the assessment of the economic impact of parasitic diseases and of their control in production animals," Vet. Parasitol., 1999, 84:145-168.
Peumans et al., "The tomato lectin consists of two homologous chitin-binding modules separated by an extensin-like linker," Biochem J., 2003, 376:717-724.
Piedrafita et al., "Increased production through parasite control: can ancient breeds of sheep teach us new lessons?" Trends Parasitol., 2010, 26:568-573.
Presland et al., "Counting nematode eggs in equine faecal samples," Vet Rec., 2005, 156:208-210.
Quiles et al., "In situ characterisation of a microorganism surface by Raman microspectroscopy: the shell of Ascaris eggs," Anal. Bioanal. Chem., 2006, 3 86:249-255.
Raikhel et al., "Structure and Function of Chitin-Binding Proteins," Annu Rev Plant Physiol Plant Mol Biol., 1993, 44:591-615.
Reece et al., "Innate Immune Responses to Lung-Stage Helminth Infection Induce Alternatively Activated Alveolar Macrophages," Infection Immunity, Sep. 2006, 74(9):4970-4981.
Reinemeyer, "Controlling Strongyle Parasites of Horses: A Mandate for Change," AAEP Proc., 2009, 55:352-360.
Reinhardt et al., "A fenbendazole oral drench in addition to an ivermectin pour-on reduces parasite burden and improves feedlot and carcass performance of finishing heifers compared with endectocides alone," J. Anim Sci., 2006, 84:2243-2250.
Robert et al., "Attitudes towards implementation of surveillance-based parasite control on Kentucky Thoroughbred farms—current strategies, awareness, and willingness-to-pay," Equine Vet. J. In Press, 2014, 34 pages.
Roberts and O'Sullivan, "Methods for egg counts and larval cultures for strongyles infesting the gastro-intestinal tract of cattle," Aust J Agric Res., 1949, 1:59-102.
Roepstorff et al., "Resistance of *Oesophagostomum* spp. in pigs to pyrantel citrate," Vet. Parasitol., 1987, 24:229-239.
Rossanigo and Gruner, "Accuracy of two methods for counting eggs of sheep nematode parasites," Vet Parasitol., 1991, 39:115-121.
Rudall and Kenchington, "The Chitin System," Biological Rev., 1973, 48:597-633.
Šafařík and Šafaříková, "Use of magnetic techniques for the isolation of cells," J Chromatography B, 1999, 722:33-53.
Scott and Horn "Zoonotic dermatoses of dogs and cats," Vet Clin North Am Small Anim Pract, Jan. 1987, 17(1):117-44.
Sendid et al., "Antibodies against Glucan, Chitin, and *Saccharomyces cerevisiae* Mannan as New Biomarkers of *Candida albicans* Infection That Complement Tests Based on *C. albicans* Mannan," Clinc Vaccine Immunol., Dec. 2008, 15(12):1868-1877.
Shen and Jacobs-Lorena, "Evolution of Chitin-Binding Proteins in Invertebrates," J Mol Evol., 1999, 48:341-347.
Siemieniewiczt and Schrempf, "Concerted responses between the chitin-binding protein secreting *Streptomyces olivaceoviridis* and *Aspergillus proliferans*," Microbiol., 2007, 153:593-600.
Skotarek et al., "Evaluation of diagnostic techniques for Anoplocephala perfoliata in horses from Alberta, Canada," Vet Parasitol., 2010, 172:249-255.
Steinfeld et al., "Livestock's Long Shadow. Environmental Issues and Options," (Rome, Italy: FAO), 2006, 416 pages.
Stoll, "On Methods of counting Nematode Ova in Sheep Dung," Parasitology, 1930, 22:116-136.
Sutherland and Leathwick, "Anthelmintic resistance in nematode parasites of cattle: a global issue?" Trends Parasitol., 2011, 27:176-181.
Suzuki et al., "Bacterial Bioreactors for High Yield Production of Recombinant Protein," J Biological Chem., Oct. 2006, 281(49):37559-37565.
Svergun et al., "Solution Structure and Conformational Changes of the Streptomyces Chitin-Binding," Biochem., 2000, 39:10677-10683.

(56) References Cited

OTHER PUBLICATIONS

USDA, "Beef 2007-08, Part IV: Reference of Beef Cow-calf Management Practices in the United States, 2007-08," Feb. 2010, 147 pages.

USDA, "Small-scale U.S. Cow-calf Operations," Apr. 2011, 27 pages.

Vadlejch et al., "Which McMaster egg counting technique is the most reliable?" Parasitol Res., 2011, 109:1387-1394.

Vidyashankar et al., "Statistical and biological considerations in evaluating drug efficacy in equine strongyle parasites using fecal egg count data," Vet. Parasitol., 2012, 185:45-56.

Waghorn et al., "Prevalence of anthelmintic resistance on 62 beef cattle farms in the North Island of New Zealand," N. Z. Vet. J., 2006, 54:278-282.

Wang and Chao, "Immobilization of Cells with Surface-Displayed Chitin-Binding Domain," Applied Environmental Microbiol., Jan. 2006, 72(1):927-931.

Ward et al., "Identification of Chitin as a Structural Component of *Giardia* Cysts," Infection Immunity, Sep. 1985, 49(3):629-6634.

Watanabe et al., "The roles of the C-terminal domain and type III domains of chitinase A1 from Bacillus circulans WL-12 in chitin degradation," J. Bacteriol., 1994, 176:4465-4472.

Wharton, "The production and functional morphology of helminth egg-shells," Parasitology, 1983, 86(Pt 4):85-97.

Wolstenholme et al., "Drug resistance in veterinary helminths," Trends Parasitol., 2004, 20:469-476.

Wood et al., "World Association for the Advancement of Veterinary Parasitology (W.A.A.V.P.) second edition of guidelines for evaluating the efficacy of anthelmintics in ruminants (bovine, ovine, caprine)," Vet. Parasitol., 1995, 58:181-213.

Zeltins and Schrempf, "Specific interaction of the *Streptomyces* chitin-binding protein CHB1 with $\alpha$-chitin: The role of individual tryptophan residues," Eur J Biochem., 1997, 246:557-564.

Zeltins and Schrempf, "Visualization of $\alpha$-chitin with a specific chitin-binding protein (CHB1) from Streptomyces olivaceoviridis," Anal. Biochem., 1995, 231:287-294.

Zhang et al., "The chitin synthase genes *chs*-1 and *chs*-2 are essential for *C. elegans* development and responsible for chitin deposition in the eggshell and pharynx, respectively," Develop Biol., 2005, 285:330-339.

"Mini Parasep Faecal Parasite Concentrator," Apacor, 2013, 4 pages.

Jurasek et al., Modification and further evaluation of a fluorescein-labeled peanut agglutinin test for identification of Haemonchus contortus eggs., Vet Parasitol, 2010, 169:209-213.

Rinaudo, "Chitin and chitosan: Properties and applications," Prog. Polym. Sci., 2006, 603-632.

Spindler et al., "Chitin metabolism: a target for drugs against parasites," Parasitol Res, 1990, 76: 283-288.

Cunliffe et al. 1953 (Egg sizes and differential egg counts in relation to sheep nematodes; Parasitology 43(3-4): 275-286) (Year: 1953).

Extended European Search Report in European Application No. 14889100.5, dated Jan. 11, 2018, 7 pages.

\* cited by examiner

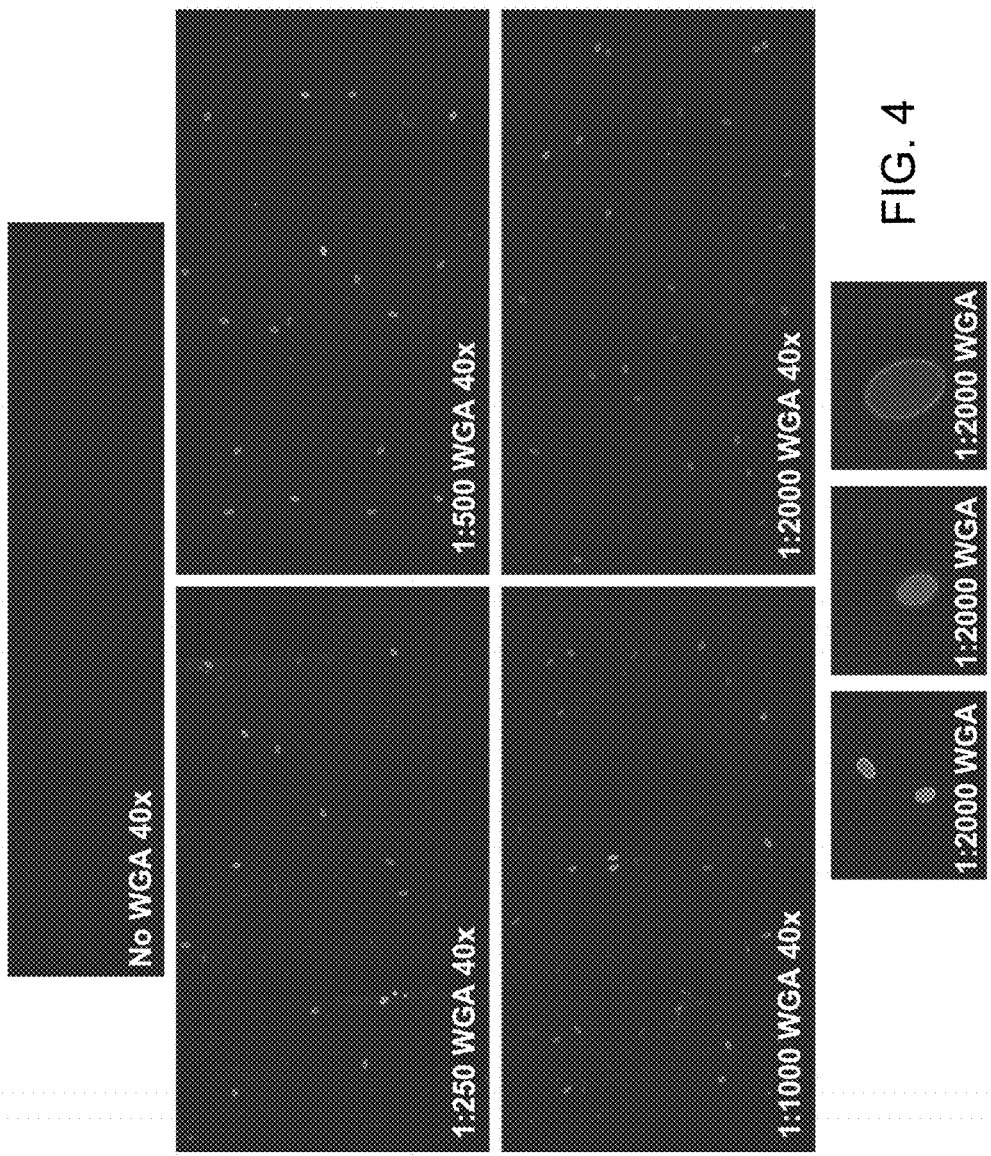

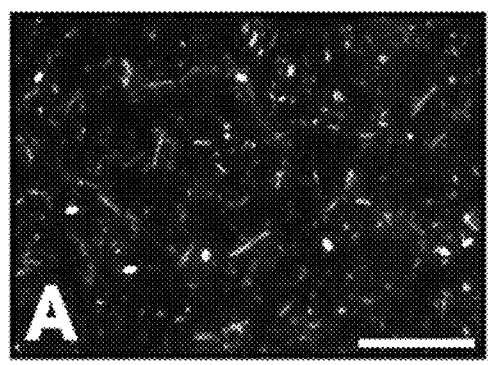
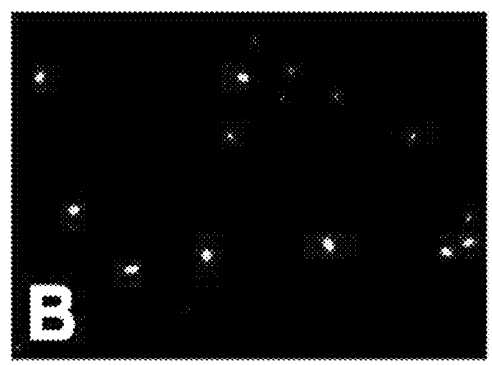
FIG. 9A    FIG. 9B
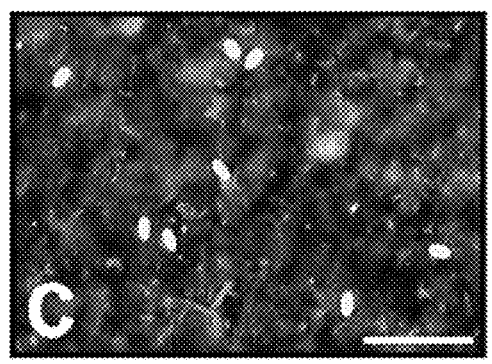
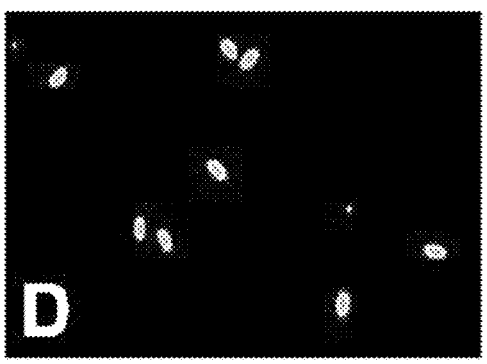
FIG. 9C    FIG. 9D

METHOD FOR THE QUANTIFICATION OF PARASITE EGGS IN FECES

CLAIM OF PRIORITY

This application claims the benefit of U.S. Provisional Patent Application No. 62/059,262, filed Oct. 3, 2014 and U.S. Provisional Patent Application Ser. No. 61/977,754, filed on Apr. 10, 2014.

TECHNICAL FIELD

This invention relates to the diagnosis of animal parasite burden, and more particularly to methods for quantifying the number of parasite eggs in feces.

BACKGROUND

Even under the most optimistic scenarios, global population is projected to continue growing well into the 21st century (UN, 2004), with the demand for meat production alone doubling between 1999 and 2050 (Steinfeld et al., 2006). One major obstacle to satisfying this demand is animal infection by internal helminth parasites, which are essentially ubiquitous in all farm animals globally.

Helminthic parasites are a polyphyletic group of worm-like animals including the taxa cestodes, nematodes, trematodes and monogeneans. Many helminthic parasites are spread via the digestive system, firstly via the ingestion of material contaminated with parasites or their eggs. During their life cycle such parasites may migrate to other parts of the body but return to the gut to produce more eggs which are then egested in the feces to provide a source for new infections.

Helminthic infection causes significant morbidity in animals, including humans, and, in the case of agricultural livestock, substantial economic loss due to reduced productivity from reduced weight gain, milk production and reproduction. Although severe infections can lead to death, ruminants carrying internal parasites, even at subclinical levels, exhibit a significant loss of productivity via a number of modalities—including anemia, decreased reproductive fitness and lactation, and reduction of food utilization—leading to reduced growth and poor body condition (Piedrafita et al., 2010; Perry and Randolph, 1999; Hoglund et al., 2001; Reinhardt et al., 2006). In the US, annual losses in livestock productivity have been estimated at three billion dollars annually (Bagley et al., 2014). In developing nations—where veterinary care, anthelmintic drugs, and regimented antihelminthic farming strategies are either less available or less widely practiced, and where food shortages are both more likely and more severe—the losses are expected to be substantially greater. Helminth infection is also an issue in agriculturally important non-ruminants, including poultry (Permin et al., 1999) and swine (Nansen and Roepstorff, 1999), and in other economically important herbivores such as horses (Duncan, 1985). In the case of horses, parasite infection also results in reduced physical performance of the animal. Internal parasite infestation, however, is not restricted to agricultural livestock and is also a problem for companion comfort animals such as cats and dogs. Infestation in cats and dogs can lead to a phenomenon called zoonosis resulting in hookworms and roundworms infecting humans' most often young children[31].

Parasitic helminthic infections are also widespread in humans. *Onchocerca volvulus*, for example, causes onchocerciasis (also known as river blindness) in humans. About 17 to 25 million people throughout the world are reported to be infected with *O. volvulus*, with approximately a million people being having some amount of loss of vision. *Brugia filariids* can infect humans and other animals, causing diseases including filariasis (including lymphatic filariasis), elephantiasis and tropical eosinophilia. Schistosomiasis is a vascular parasitic disease in humans caused by blood flukes of the *schistosoma* species. Schistosomiasis is one of many helminthic diseases infecting over a billion people worldwide. These diseases include ascariasis, trichuriasis, enterobiasis, filariasis, trichinosis, onchocerciasis, fascioliasis, and cysticercosis. Schistosomiasis ranks second to malaria as a major cause of morbidity and suffering due to parasites.

Compounding the above problems, resistance to commonly used dewormers (anthelmintic resistance) is a global and growing problem in livestock production (Kaplan, 2004). Multidrug resistance is a common phenomenon in sheep and goat operations (da Cruz et al., 2010), with several cases of total anthelmintic failure reported (Cezar et al., 2010; Howell et al., 2008). Similarly, equine parasites have been documented to be resistant to all classes of dewormer currently available on the market, and the overwhelming majority of equine operations are facing resistance to at least one drug class (Peregrine et al., 2014). Most recently, cattle parasites have been found increasingly resistant to several classes of commonly used anthelmintic products (Gasbarre et al., 2009; Waghorn et al., 2006; Jackson et al., 2006).

Moreover, this resistance appears to be evolving at a significantly faster rate than that at which new dewormer products are being developed and launched: no new anthelmintic drug classes have been launched for use in large animals in North American since the early 1980s. For these reasons, veterinary organizations world-wide are promoting the monitoring of parasite infection and the presence of drug resistance as a critical aspect of animal care (Wood et al., 1995).

In the area of veterinary medicine, helminth infection is sometimes diagnosed by manifested clinical symptoms. The central tool in the practice of veterinary parasitology is the fecal egg-count (FEC), which has remained relatively unchanged for almost a century[4,11] and, in general, rely on the flotation of eggs in a sugar and/or salt medium that is denser than the eggs themselves, followed by microscopic examination and manual counting. Two FEC methods are currently in use.

The first, and perhaps the most universally used egg-counting procedure is the McMaster slide counting method, originally developed with sheep feces by Gordon and Whitlock in 1939. In this method, the fecal matter is suspended in a sugar and/or salt (SS) solution of greater density than the parasitic eggs themselves and placed in a microscopic slide especially fabricated for the purpose (the McMaster slide counting method). The eggs float to the surface (thereby separating them from the denser fecal debris to facilitate visualization) and are counted manually by a trained individual using a microscope at a 40-100× magnification.

A second, commonly used egg-counting procedure is the Wisconsin method and its derivatives. For these methods, eggs are floated directly, usually under the influence of a centrifugal field but also by gravity, onto a coverslip placed on the surface meniscus of the flotation medium. Sensitivity can be improved by sampling more of the fecal suspension by placing it in a tube to form a meniscus. The meniscus is overlaid with a coverslip and then subjected to centrifugation in a swing-out rotor (Rossanigo and Gruner, 1991;

Egwang and Slocombe, 1981). Eggs adhering to the coverslip can then be counted microscopically as before.

While McMaster-type assays are simpler to perform, the high dilutions and small samplings involved result in assays with higher variability and lower sensitivity than Wisconsin-type tests. Conversely Wisconsin tests recover more of the eggs because of the increased flotation produced by centrifugal fields and also the large sample volumes they permit, but are technically slightly more demanding and require access to a centrifuge, which is impractical for many veterinary practices and in the field.

Unfortunately both of these techniques are not only time-consuming but also require the use of specialized laboratory equipment (i.e., a microscope, with or without a centrifuge), which is seldom available to veterinarians on-site, much less to the animal owners. Furthermore, the majority of animal owners do not possess the required training to reliably examine such samples (e.g., a layman might easily confuse the eggs with other fecal particulates such as pollen grains). Generally samples are collected and either sent to the veterinarian's office for analysis or to a third-party analytical laboratory, resulting in added cost and/or delays in diagnosis times. Alternatively, owners can ship the feces direct to laboratories via a number of commercial services but generally need to wait 48 hours for results. This, coupled to time-consuming nature of the tests and the requirement of trained personnel to process and inspect each sample, with a concomitant impact on cost, results in fewer animal owners routinely testing their livestock for the presence of parasites and the development of resistance.

In addition to the time and equipment issues, current egg-count methods suffer from a number of technical drawbacks. For example, egg-count variability limits the effectiveness of current egg-count methods. Equine egg counts have been estimated to vary by +/−50% between repeated counts (partially due to subjective inter-analyst variability, and partly for statistical reasons due to small sampling volumes). Thus, delineating between a true change and chance variability in fecal egg-count reduction is a real challenge (Vidyashankar et al., 2012). Although variability can be reduced by better analyst training, performing repeated counts, or using methods with lower detection limits, all of these solutions come with a cost in either additional training or processing time. Another drawback are egg loss rates. A certain percentage of eggs in a sample remains trapped in the fecal debris and does not make it to the flotation step. Depending on the technique and the operator, the egg loss rate has been found to vary between 30 and 60% (Vidyashankar et al., 2012). Importantly the detection limit, the lowest egg count detectable by the given technique, provides a technical limitation to the known methods. It is typically within the range of 1-50 eggs-per-gram (EPG). McMaster techniques (see FIG. 1) usually have detection limits of 25 or 50 EPG, making it very difficult to detect low egg count levels, which is particularly important for resistance testing (Vidyashankar et al., 2012).

As a result, prophylactic treatment with anthelmintic drugs has become standard across the industry. Unfortunately, and analogous to the over-prescription of antibiotics, the rising frequency of drug resistant nematodes is a growing global concern across all species, particularly small ruminants (Kaplan, 2004; Wolstenholme et al., 2004; Sutherland and Leathwick, 2011; Jackson and Coop, 2000; Roepstorff et al., 1987; Coles et al., 2003; Cernanska et al., 2006; Kornele et al., 2014). Both veterinary and regulatory organizations have now officially recognized this rapidly growing problem and have issued guidelines to (1) help monitor the growth of such resistance, and (2) attempt to curtail it by reducing the current indiscriminative use of both prescription and over-the-counter anthelmintic drugs (Wood et al., 1995; EMEA, 2006; FDA, 2014).

Unfortunately, monitoring for the development of resistance by observing Fecal Egg Count Reduction (FECR) involves the use of egg flotation methods, with the disadvantages described above[8]. Thus, these methods are unlikely to be widely used. To underscore this supposition, a recent survey of Kentucky thoroughbred farms showed that most respondents were aware of, and concerned about, the phenomenon of drug-resistant parasites; yet, over 70% were still deworming prophylactically (Robert et al., 2014). In addition, research from USDA has shown that 50-70% of cattle farmers agree that internal parasites have a significant economic impact on their operations (USDA, 2011b); yet, only 0.7% make use of any type of laboratory testing for this problem (USDA, 2010). In summary, the inconvenience of fecal egg counting appears to represent a significant barrier to the widespread adoption of a more targeted approach to the treatment and management of parasite infection.

While regulatory authorities in Europe have recognized the threat of the emergence drug resistant strains and moved to restrict their availability, in the United States many of these drugs are currently still openly available to the public over-the-counter. As a result, the use of fecal egg count reduction tests (FECRs) have been recommended by veterinary professional associations. FECRs depend upon systematically assessing parasite burden using egg counts as a surrogate marker of parasite load both before and after treatment with anti-helminthic drugs. Development of resistance can be detected by a lower-than-expected drop in egg counts after treatment, prompting appropriate managed responses to mitigate the proliferation of resistant strains through the population. As a result the fecal egg count has grown increasingly more important, while surprisingly very little progress has been made in improving this clinically important diagnostic tool.

Despite the passage of almost a century and the development of sophisticated modern analytical methodologies in other areas, the practice of egg counting has remained relatively unchanged, with the majority of innovations restricted to modifications in the flotation media or to methods for collecting eggs from larger fecal samples. For example, the volume of flotation chambers have been enlarged to improve sensitivity[14,15,18], or alternative flotation solutions have been explored[14,17].

Some workers have made efforts to develop more sophisticated efforts to either detect or quantify eggs in feces, using methods such as the Polymerase Chain Reaction (Demeler et al., 2013; Learmount et al., 2009) and flow cytometry (Colditz et al., 2002). However, such sophisticated techniques, along with the expertise and equipment required to conduct them, make them even more impractical as tools for anything other than research purposes.

Although some efforts have been made towards discovering egg-surface probes to aid in detection, these efforts have been limited to the screening of various lectins, in order to determine species of eggs to which these lectins can bind. Once determined, these proteins can be used as species-specific markers for the detection (but not quantification) of the presence of certain species or genera (Palmer and McCombe, 1996; Hillrichs et al., 2012; Colditz et al., 2002). However, because total egg count remains the standard for clinical decision making and for monitoring anthelmintic resistance, it remains to identify a marker that is generic for all helminth eggs. The identification of such a ubiquitous and experimentally tractable marker would open up the possibility of utilizing it to develop a rapid quantitative method to enumerate total fecal egg load and thus supplant flotation methods and their associated shortcomings.

Unfortunately, little work has been carried out to elucidate the molecular composition of clinically relevant egg surfaces, and what little that has been done has yielded little specific information (Wharton, 1983; Quiles et al., 2006).

Parasitic protozoal infections are also responsible for a wide variety of diseases of medical and veterinary importance, ranging across malaria and *Pneumocystis carinii* pneumonia in man and various coccidioses in birds, fish and mammals. Many of the diseases are life threatening to the host and cause considerable economic loss in animal husbandry. Coccidiosis is a protozoan parasitic disease that affects the intestinal tract of animals including, but not limited to, cattle, sheep, goats, rabbits, pigs, chickens, turkeys, cats, and dogs. Parasites of interest include, but are not limited to *Isospora* sp. (dogs and cats); *Eimeria maxima*, *E. acervulina*, *E. brunetti*, *E. necatrix*, and *E. tenella* (chickens); *E. meleagridis*, *E. gallopavonis*, *E. adenoeides*, and *E. dispersa* (turkeys); *E. bovis* (cattle); *E. ovina* (sheep); *E. porci* (pigs); and *E. stiedai* (rabbits). Coccidiosis is one of the most economically important diseases in many livestock species. The disease is characterized by diarrhea, unthriftiness, loss of appetite and weight, and variable levels of mortality. In lifestock animals, economic losses are caused by a decreased weight gain due in part to the malabsorption of nutrients through the gut wall. And, as with helminth infections, the state of the art for detecting protozoan oocysts relies on time-consuming methods.

While many parasites spend part of their lifecycle in the gastrointestinal tract and are egested in feces, many other parasites infect the bladder and kidneys the host animal. *Pearsonema plica* and *Dioctophyme renale* are two such parasites known to infect the bladder and kidney in dogs. Eggs of both genera can be found in urine samples. Schistosomiasis species may infect the urinary tract or intestines, the eggs of which may be found in the animal's urine or stool.

As can be seen, although more modern methods have been developed, these tests have not been widely adopted and manual egg counting has remained the most widely available and routinely used method to monitor internal parasite infestation (i.e., helminth and protozoan parasite infestation). Thus, a need exists for a simple, accurate and cost-effective method for quantifying the number of parasite eggs in feces that can be performed by either veterinarians in the field or by animal owners themselves.

SUMMARY

The present invention is based on the use of N-acetyl-D-glucosamine (GlcNac) binding domain (e.g., GlcNac binding proteins) and fragments thereof for the detection of helminth eggs in environmental samples (e.g., a fecal sample). "Detect" refers to identifying the presence, absence or amount of the object to be detected. The amount detected can be none or below the level of detection. The invention provides a simple on-site test which will allow both veterinarians and animal owners to diagnose the presence and levels of helminth parasite infection and/or parasitic protozoal infections, thereby allowing them to more appropriately and efficiently tailor treatment and preventative strategies to their specific needs. The test can also be used in a more controlled laboratory setting. This document outlines general principles for moving parasite egg counting away from the microscope, where they have languished for more almost a century, and describes specific assays that achieve this aim using modern biochemical techniques.

The methods disclosed herein offer further improvements to current egg counting methods; namely, the approach will enable (1) sample throughput to be increased and will eliminate subjectivity, thereby reducing or eliminating these sources of variation; (2) the optional elimination of the flotation step, which could at least partially ameliorate the problem of egg loss rates; and (3) concentration of the fecal sample by filtration, which would greatly improve sensitivity. In addition, the technology would enable the tests to be performed rapidly on-site, thereby eliminating the time- and inconvenience-cost of transporting feces to a laboratory and the processing time once there. Finally, the technology will fit well into established veterinary practice, as total FEC (regardless of parasite species) is the most commonly used metric for informing clinical treatment decisions (Coles et al., 2006; Nielsen et al., 2010).

Thus, in one aspect, the invention provides methods for detecting the presence or absence of helminth eggs and/or protozoan oocysts in an environmental sample (e.g., in a fecal sample, a urine sample, a water sample, a waste water or sewage sample or a soil sample). In some aspects, the invention provides methods for detecting the presence or absence of helminth eggs and/or protozoan oocysts in an environmental sample, the methods comprising obtaining a solution comprising an environmental sample suspended in a sample buffer, flowing the fecal solution through two or more (e.g., two, three, four, five, six, seven eight, nine, ten, twenty, or fifty) filters of decreasing pore size, the number and pore sizes being determined by the species of animal from which the feces is obtained and by the types of eggs and/or oocyts being detected.

In some aspects, the invention provides methods for detecting the presence or absence of helminth eggs and/or protozoan oocysts in fecal samples, the methods comprising obtaining a fecal solution comprising a fecal sample suspended in a sample buffer, flowing the fecal solution through two or more (e.g., two, three, four, five, six, seven eight, nine, ten, twenty, or fifty) filters of decreasing pore size, the number and pore sizes being determined by the species of animal from which the feces is obtained and by the types of eggs and/or oocyts being detected.

As used herein, the terms "one or more" and "at least one" are used interchangeably and mean one, two, three, four, five, six, seven eight, nine, ten, twenty, fifty, etc, of the item to which "one or more" or "at least one" refers. The term "two or more" means at least two, more suitably, two, three, four, five, six, seven eight, nine, ten, twenty, fifty, etc, of the item to which "two or more" refers.

Therefore in one aspect, the solution comprising an environmental sample (e.g., a fecal solution comprising a fecal sample) is flowed through a first filtration membrane having a pore size of between about 85 microns and about 350 microns, between about 100 microns and about 300 microns, between about 125 microns and about 250 microns, or between about 150 microns and about 200 microns to form a first filtrate, flowing the first filtrate through a second filtration membrane having a pore size of between about 1 and about 10 microns, 5 microns and about 45 microns, between about 10 microns and about 45 microns, between about 15 microns and about 45 microns, between about 20 microns and about 45 microns, between about 25 microns and about 40 microns, or between about 30 microns and about 35 microns, contacting helminth eggs captured on the second filtration membrane with a N-acetyl-D-glucosamine binding domain or fragment thereof, such as, for example a lectin, a chitinase, a chitin binding domain (CBD) or other a N-acetyl-D-glucosamine binding protein or fragments thereof conjugated to a detectable moiety, and detecting the presence or absence of helminth eggs in the fecal sample based on the detectable moiety, e.g., the intensity of the signal of the detectable moiety.

The terms "first," "second" and "third" are used in this disclosure in their relative sense only. It will be understood that, unless otherwise noted, those terms are used merely as a matter of convenience in the description of one or more of the embodiments. The terms "first," "second" and "third" are only used to distinguish one element from another element, and the scope of the rights of the disclosed technology should not be limited by these terms. For example, a first element may be designated as a second element, and similarly the second element may be designated as the first element.

In another aspect, the invention provides methods for detecting the presence or absence of helminth eggs and/or protozoan oocysts in an environmental sample (e.g., a fecal sample) comprising obtaining a solution comprising an environmental sample sample (e.g., a fecal solution comprising a fecal sample) suspended in a sample buffer, flowing the fecal solution through a first filtration membrane having a pore size of between about 85 microns and about 350 microns, between about 100 microns and about 300 microns, between about 125 microns and about 250 microns, or between about 150 microns and about 200 microns to form a first filtrate, flowing the first filtrate through a second filtration membrane having a pore size of between about 1 and about 10 microns, 5 microns and about 45 microns, between about 10 microns and about 45 microns, between about 15 microns and about 45 microns, between about 20 microns and about 45 microns, between about 25 microns and about 40 microns, or between about 30 microns and about 35 microns, contacting a sample captured on the second filtration membrane with a first reagent comprising a chitin-binding dye which fluoresces under fluorescence-exciting light, illuminating the sample captured on the second filtration membrane with fluorescence-exciting light; and examining the fluorescence of the sample to determine the presence or absence of helminth eggs and/or protozoan oocysts in the sample based on the fluorescent intensity or number of fluorescent particles.

In yet another aspect, the invention provides methods for detecting the presence or absence of helminth eggs and/or protozoan oocysts in an environmental sample (e.g., a fecal sample) comprising obtaining a solution comprising an environmental sample (e.g., a fecal solution comprising a fecal sample) suspended in a sample buffer, flowing the solution through a first filtration membrane having a pore size of between about 85 microns and about 350 microns, between about 100 microns and about 300 microns, between about 125 microns and about 250 microns, or between about 150 microns and about 200 microns to form a first filtrate, flowing the first filtrate through a second filtration membrane having a pore size of between about 1 and about 10 microns, 5 microns and about 45 microns, between about 10 microns and about 45 microns, between about 15 microns and about 45 microns, between about 20 microns and about 45 microns, between about 25 microns and about 40 microns, or between about 30 microns and about 35 microns, contacting helminth eggs and/or protozoan oocysts captured on the second filtration membrane with a first reagent comprising a lectin or a CBD or a N-acetyl-D-glucosamine binding protein or fragments thereof to form a first reagent sample, contacting the first reagent sample with a second reagent comprising an antibody that specifically binds to the lectin or CBD, wherein the antibody is conjugated to a detectable moiety, and determining the presence or absence of helminth eggs and/or protozoan oocysts in the sample based on the detectable moiety.

In some embodiments, the environmental sample is a fecal sample. The step of obtaining a fecal solution can comprise suspending a fecal sample in a sample buffer to form a first fecal solution, and flowing the first fecal solution through a bulk filtration membrane having a pore size of between about 400 microns and about 800 microns, between about 425 microns and about 750 microns, between about 450 microns and about 700 microns, between about 500 microns and about 650, or between about 550 microns and about 600 microns to provide the fecal solution. In one embodiment, the bulk filtration membrane has a pore size of between about 400 microns and about 450 microns, the first filtration membrane has a pore size of between about 85 microns and about 120 microns, and the second filtration membrane has a pore size of between about 20 microns and about 40 microns. Flowing the first fecal solution through the bulk filtration membrane serves to remove larger particles and debris from, allowing for more efficient filtration through the first and second filtration membranes.

In some embodiments, the methods further comprising, after flowing the solution through a second filtration membrane, suspending helminth eggs and/or protozoan oocysts captured on the second filtration membrane in a liquid sample buffer.

According to a further aspect, the methods disclosed herein further comprise treating the sample (e.g., the environmental) with an oxidizing agent or bleach solution prior to the contacting step. Thus, in some embodiments, the contacting step is preceded by treating the sample with a bleach solution.

In some embodiments, the GlcNac binding domain is a GlcNac binding protein selected from the group consisting of a lectin, a chitinase or a chitin binding domain (CBD), or fragments thereof. More particularly, the lectin can be any lectin capable of binding N-acetyl-D-glucosamine, including, a lectin selected from the group consisting of wheat germ agglutinin (WGA), soybean agglutinin (SBA), *Maclura pomifera* lectin (MPL), *Bauhinia purpurea* lectin (BPL), *Datura stramonium* lectin (DSL), *Lycopersicon esculentum* lectin (LEL), *Solanum tuberosum* lectin (STL) and *Psophocarpus tetragonolobus*-II (PTL-II). In one embodiment, the lectin is wheat germ agglutinin (WGA).

In some embodiments, the GlcNac binding protein is conjugated to a solid support such as magnetic or non-magnetic beads or to a membrane such as nitrocellulose or polyvinylidine difluoride which can be used to capture and concentrate the eggs either in combination with or instead of filtration.

In some embodiments, the GlcNac binding protein is conjugated to a detectable moiety selected from the group consisting of a hapten, an enzyme, an antibody epitope, an antigen, a fluorophore, a radioisotope, a nanoparticle, a member of a binding pair, and a metal chelate. For example, the detectable label may be a first member of a binding pair, wherein the binding pair is selected from the group consisting of biotin/streptavidin, biotin/avidin, biotin/neutravidin, biotin/captavidin, epitope/antibody, protein A/immunoglobulin, protein G/immunoglobulin, protein L/immunoglobulin, GST/glutathione, His-tag/Metal (e.g., nickel, cobalt or copper), antigen/antibody, FLAG/M1 antibody, maltose binding protein/maltose, calmodulin binding protein/calmodulin, enzyme-enzyme substrate, and receptor-ligand binding pairs. In one embodiment, the detectable moiety is a first member of a binding pair. In some embodiments, a first member of the binding pair is conjugated to the N-acetyl-D-glucosamine binding protein and the second member of the binding pair is immobilized on a solid support.

In some embodiments, the detectable moiety is a first member of a binding pair; and the second member of the binding pair is conjugated to an enzyme, an antibody epitope, an antigen, a fluorophore, a radioisotope, a nanoparticle, a member of a second binding pair, and a metal chelate.

In yet another embodiment, the detectable moiety is a first member of a binding pair, wherein the first member of the binding pair is biotin and the second member of the binding pair is selected from the group consisting of streptavidin, avidin, neutravidin and capravidin, and the second member of the binding pair conjugated to an enzyme.

In some embodiments, the detectable moiety is a fluorophore is selected from the group consisting green fluorescent protein, blue fluorescent protein, red fluorescent protein, fluorescein, fluorescein 5-isothiocyanate (FITC), cyanine dyes (Cy3, Cy3.5, Cy5, Cy5.5, Cy7), Bodipy dyes (Invitrogen) and/or Alexa Fluor dyes (Invitrogen), dansyl, Dansyl Chloride (DNS-Cl), 5-(iodoacetamida)fluorescein (5-IAF, 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, rhodamine dyes (5-carboxyrhodamine 6G hydrochloride, Lissamine rhodamine B sulfonyl chloride, rhodamine-B-isothiocyanate (RITC (rhodamine-B-isothiocyanate), rhodamine 800); tetramethylrhodamine 5- (and 6-)isothiocyanate (TRITC)), Texas Red™, sulfonyl chloride, naphthalamine sulfonic acids including but not limited to 1-anilinonaphthalene-8-sulfonic acid (ANS) and 6-(p-toluidinyl)naphthalen-e-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, Naphtyl Styryl, 3,3'dipropylthiadicarbocyanine (diS-C3-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, IR-125, Thiazole Orange, Azure B, Nile Blue, Al Phthalocyanine, Oxaxine 1,4',6-diamidino-2-phenylindole. (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors and Coronene.

In some embodiments, the detectable moiety is an enzyme that catalyzes a color change reaction, including, an enzyme selected from the group consisting of alkaline phosphatase, beta-galactosidase, horse radish peroxidase, urease and beta-lactamase and glucose oxidase.

In some embodiments, the GlcNac binding protein is wheat germ agglutinin and the detectable moiety is fluorescein.

The signal intensity of the detectable label can be measured using instruments and devices known to those skilled in the art, including, for example a portable or benchtop fluorometer (e.g., a handheld fluorometer) or a portable or benchtop colorimeter (e.g., a handheld colorimeter). The signal intensity of the detectable moiety can be determined by visual inspection. In some embodiments, the signal intensity of the detectable moiety in determined using an imaging device appropriate for visualizing the selected detectable moiety. In some embodiments the imaging device is a digital camera, a mobile phone, a smartphone, a tablet, a portable computer, a computer, or a scanner.

In some embodiments, the methods further comprise enumerating the helminth eggs in the fecal sample. In one embodiment, the methods comprise enumerating the helminth eggs in the fecal sample is performed using a microscope.

In some embodiments, contacting a sample captured on the second filtration membrane with a first reagent comprising a chitin-binding dye which fluoresces under fluorescence-exciting light, wherein the chitin-binding dye which fluoresces under fluorescence-exciting light is selected from the group consisting of calcofluor white, Uvitex 3B (distyryl biphenyl fluorescent whitening agent), Rylux BA, Rylux BSU (1,4-benzenedisulfonic acid-2,2'-[ethyleneidylbis[(3-sulpho-4,1-phenylene)imino[6-bis(2-hydroxyethyl)amino]-1,3,5-trihexasodium salt) (Ostacolor, Pardubice, Czech Republic) and Blankophor (disodium 4,4'-bis {(4-anilino)-6-morpholino-1,3,5-triazin-2-yl)amino}stilbene-2,2'-disulphonate).

In some aspects, the disclosure provides methods for detecting the presence or absence of helminth eggs or protozoan oocysts in an environmental sample, the method comprising obtaining a solution comprising an environmental sample suspended in a sample buffer; flowing the solution through a first filtration membrane having a pore size of between about 85 microns and about 350 microns to form a first filtrate; flowing the first filtrate through a second filtration membrane having a pore size of between about 5 microns and about 45 microns; contacting helminth eggs captured on the second filtration membrane with a N-acetyl-D-glucosamine binding protein or fragment thereof conjugated to a detectable moiety; and detecting the presence or absence of helminth eggs or protozoan oocysts in the environmental sample based on the signal intensity of the detectable moiety.

In some aspects, the disclosure provides methods for determining the presence or absence of helminth eggs or protozoan oocysts in an environmental sample, the method comprising: obtaining a solution comprising an environmental sample suspended in a sample buffer; flowing the solution through a first filtration membrane having a pore size of between about 85 microns and about 350 microns to form a first filtrate; flowing the first filtrate through a second filtration membrane having a pore size of between about 5 microns and about 45 microns; contacting a sample captured on the second filtration membrane with a first reagent comprising a chitin-binding dye which fluoresces under fluorescence-exciting light; illuminating the sample captured by the second filtration membrane with fluorescence-exciting light; and assessing the fluorescence of the sample to determine the presence or absence of helminth eggs or protozoan oocysts in the environmental sample based on the fluorescence intensity or number of fluorescent particles.

In some aspects, the disclosure provides methods for determining the presence or absence helminth eggs or protozoan oocysts in an environmental sample, the method comprising: obtaining a solution comprising an environmental sample suspended in a sample buffer; flowing the solution through a first filtration membrane having a pore size of between about 85 microns and about 350 microns to form a first filtrate; flowing the first filtrate through a second filtration membrane having a pore size of between about 5 microns and about 45 microns; contacting helminth eggs captured on the second filtration membrane with a first reagent comprising a N-acetyl-D-glucosamine binding protein or fragment thereof to form a first reagent sample; contacting the first reagent sample with a second reagent comprising an antibody that specifically binds to the N-acetyl-D-glucosamine binding protein, wherein the antibody is conjugated to a detectable moiety; and determining the presence or absence of helminth eggs or protozoan oocysts in the fecal sample based on the intensity of the detectable moiety.

In some embodiments, the environmental sample is a fecal sample. Accordingly, obtaining the solution comprises suspending a fecal sample in a sample buffer to form a first fecal solution; and flowing the first fecal solution through a bulk filtration membrane having a pore size of between about 400 microns and about 800 microns to obtain the solution comprising the fecal sample.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 4 shows chitin specific helminth egg staining obtained with FITC labeled wheat germ agglutinin (WGA).

FIGS. 9A-9D shows images of CBD-Fluorescein stained eggs. Eggs were imaged with either an 8 MP iPhone 5s (A, B) or with a 16 MP Olympus PE2 Pen camera (C, D). Images are shown both raw (A, C) or after processing to remove background (B, D). Bar (A)=1 mm, Bar (B)=0.5 mm.

DETAILED DESCRIPTION

The following disclosure describes novel methods for detecting the presence or absence of helminth eggs and/or protozoan oocysts in environmental samples (e.g., in a fecal sample, a urine sample, a water sample, a waste water or sewage sample or a soil sample). For ease of review, exemplary methods and kits for detecting the presence or absence of helminth eggs and/or protozoan oocysts in fecal samples are provided for illustrative purposes and are not intended to limit the scope of the invention, which is defined by the scope of the appended claims.

Figure 5:
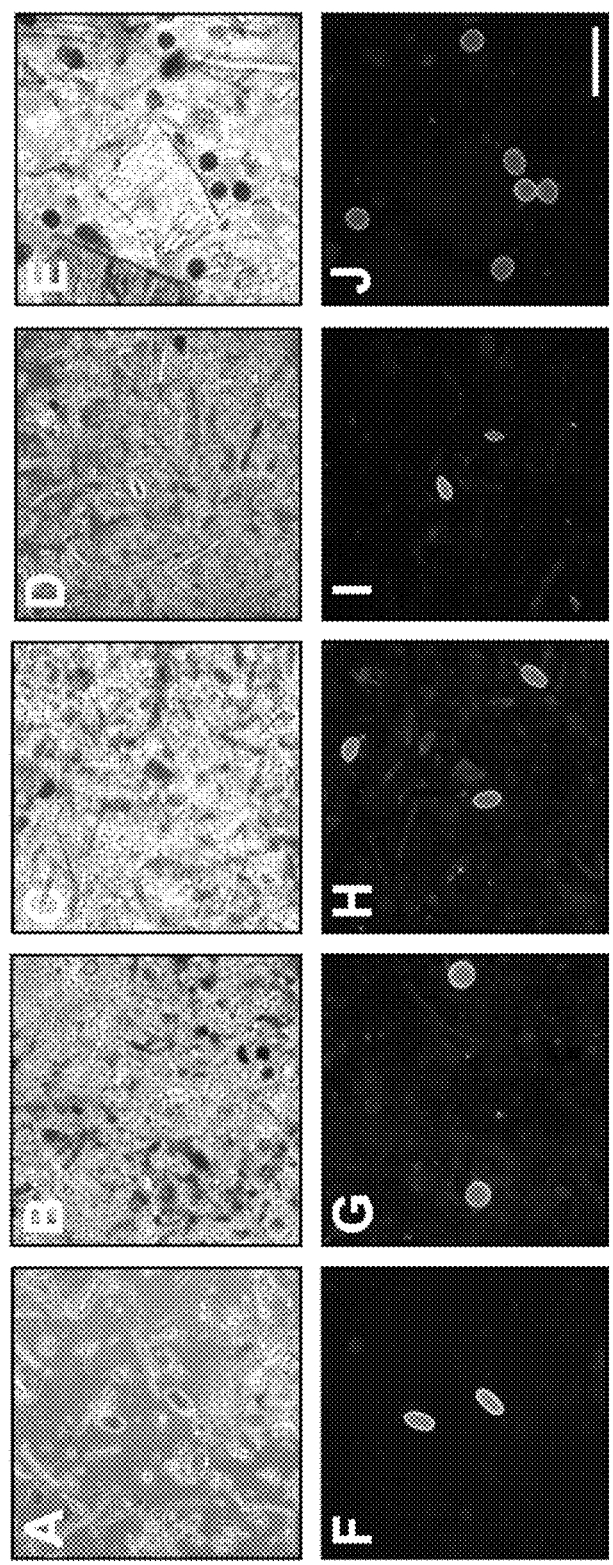
FIGS. 5A to 5J show staining of helminth eggs with CBD conjugated to fluorescein. (samples imaged in phase contrast (A-E) or fluorescence mode (F-J). Bar=200 microns.

Although chitin has been described as being a component of some helminth eggs and protozoan oocysts, it has never been generally acknowledged to be a universal component of such eggs. At least in part, the present invention is based on the discovery by the inventors that that chitin can serve as a generic marker for most, if not all, helminth parasite eggs (see, e.g., FIG. 5) and/or protozoan oocyst and thus form a basis for a test to determine total parasitic load. Chitin is a linear polymer structurally similar to cellulose, but consisting entirely of β1-4 linked units of N-acetyl glucosamine (GlcNAc) rather than glucose (Rudall and Kenchington, 1973). Behind cellulose, it is the most abundant biopolymer in nature, the major constituent of the exoskeletons of both terrestrial and aquatic arthropods, and a critical component of the cell walls of fungi and (to a lesser extent) yeast. Chitin's universal role as a structural component of biological matrices and the similar appearance of the surface of most helminth eggs, suggests that it may be a ubiquitous marker for parasite eggs.

The presence of chitin can be probed not only semi-specifically with various GlcNAc recognizing lectins and various small molecule-fluorophores, but also more stringently with truncated versions of various chitinases consisting of their respective chitin binding domains (CBDs) (Hardt and Laine, 2004; Hashimoto et al., 2000; Gao et al., 2002; Arakane et al., 2003; Chu et al., 2001; Kolbe et al., 1998; Zeltins and Schrempf, 1995). Thus, the inventors hypothesized that the detection of helminth eggs from fecal samples could be accomplished either (1) colorimetrically, by attaching an enzymatic reporter to GlcNAc binding protein to generate a signal upon the addition of an appropriate substrate; or (2) fluormetrically by conjugating the GlcNAc binding protein with an appropriate fluorophore.

Although CBDs and lectins exhibit higher binding affinities to chitin and GlcNAc containing sugar structures, they can also bind to other carbohydrate polymers, notably cellulose, which is a major component of the feces of herbivores and omnivores. The data available in the literature is variable and sometimes contradictory[26-30], making it unclear whether such proteins could discriminate between eggs and the vast bulk of the remaining feces. The inventors have discovered that such proteins can indeed be used to detect eggs over this background material and so form the basis of methods to enumerate them.

Provided herein are methods and the associated hardware for detecting presence or absence of helminth parasite eggs or protozoan oocysts in an environmental sample. Notably, the methods provided herein utilized a filtration process comprising flowing an environmental sample through a first filtration membrane having a pore size of between about 85 microns and about 350 microns, between about 100 microns and about 300 microns, between about 125 microns and about 250 microns, or between about 150 microns and about 200 microns to form a first filtrate; flowing the first filtrate through a second filtration membrane having a pore size of between about 1 and about 10 microns, 5 microns and about 45 microns, between about 10 microns and about 45 microns, between about 15 microns and about 45 microns, between about 20 microns and about 45 microns, between about 25 microns and about 40 microns, or between about 30 microns and about 35 microns; contacting helminth eggs and protozoan oocysts captured on the second filtration membrane with a reagent which binds chitin or N-acetyl-D-glucosamine; and detecting the presence or absence of helminth eggs or protozoan oocysts in the environmental sample by observing, quantitatively or qualitatively, the degree to which the reagent which binds chitin or N-acetyl-D-glucosamine has bound to of helminth eggs or protozoan oocysts in the environmental sample. The environmental sample may be any sample suspected of containing helminth eggs or protozoan oocysts, including, for example a fecal sample, a water sample, a waste water or sewage sample or a soil sample.

The disclosure also provides methods and the associated hardware for enumerating helminth parasite eggs and/or protozoan oocysts in the sample. The disclosed methods move away from parasite egg counting methods using a microscope, where they have languished for a century or more, and describes specific methods for using modern biochemical techniques.

Eggs can be detected in a suspension of animal feces in water or other suitable liquid (including buffered solutions) by a two-step process; egg capture and egg detection. In one step, eggs are captured onto a solid substrate as a means of isolating them from fecal debris. The substrate may be two- or three-dimensional, and may itself be co-suspended in the liquid in the form of, for example, beads or particles.

Egg capture is facilitated by coating the substrate with molecules such as proteins, carbohydrates or activated chemical groups that can interact with the surface of the eggs. If necessary capture can be facilitated by pretreating the fecal suspension with chemicals to expose or activate chemical groups on the eggs that could facilitate the capture. Such chemicals include, but are not limited to, bleach, surfactants, oxidizing agents chaotropic agents and enzymes.

Capture can be specific, using as non-limiting examples, antibodies against egg components (e.g., GlcNac) or lectins that recognize only structures on either all parasite eggs, or parasite eggs of certain taxonomic groups or particular species. Alternatively, capture can be non-specific and provide a way to separate eggs from the particulate fecal debris, but not necessarily all of the fecal components. Such capture could be achieve, as non-limiting examples, by chemically reactive groups such as N-ethyl-maleimide esters, N-hydroxysuccinamide esters, amines in the presence of cross-linking agents such as carbodiimides, aldehydes and others. Alternatively such capture could be achieved by macromolecules such as proteins or carbohydrates that recognize both parasite eggs, but also other components of the feces.

Capture onto a substrate need not be dependent on specific chemicals to bind the eggs and can also be achieved by physical methods, for example filtration where eggs can be separated from large fecal particles by filtration through, as a non-limiting example, a 100 micron filter. Filtrate containing eggs can then be passed through a smaller filter (for example 10-40 micron μm) to trap the eggs while removing smaller particles including spores and fungi (which could interfere with egg detection if the detection reagent can also bind to these cells). Eggs captured on the filter can then be detected and quantified as described elsewhere. Alternatively, eggs can be captured and isolated from the feces without using a solid substrate. For example, large fecal particles could be removed by a slow-speed centrifugation and the eggs harvested from the supernatant by a faster spin which nevertheless is too slow to sediment smaller particles and yeast or fungi. Other physical methods such as diffusion, electrophoresis, chromatography or density separation can also be used to isolate eggs prior to detection.

The method of egg detection depends on whether the capture was specific or non-specific. If the capture step was specific then selection of the detection method is less stringent since contaminating fecal components would have been removed (for example, capturing eggs using magnetic beads coated with CBD, and then using fluorescent dye that binds both chitin and other sugar polymers such as cellulose for detection, for example cacofluor white). If capture was non-specific or semi-specific, and also entrapped non-egg components then the detection must be specific enough to discriminate between the eggs and the contaminants. Possible, non-limiting detection methods include: visual inspection; attachment and then optical detection of molecules specific to the eggs themselves such as antibodies, chitin binding domains, lectins or other proteins, all conjugated to suitable reporter groups such as fluorophores, chromophores, enzymes, colored microparticles, quantum dots, or colloidal metals. Chemical methods for detecting general cellular components can also be used, and these include methods to detect proteins, carbohydrates, lipids and nucleic acids using assays known to those skilled in the art. Additionally hybridization of egg DNA or RNA to specific probes, or amplification of such nucleic acids by PCR) can also be used following its release from the eggs. Physical methods can also be used to provide specificity in detection (following, if necessary, release of the eggs from the substrate) and non-limiting examples of such methods include centrifugation, filtration, flotation or particle counting (for example, using devices such as coulter counters, cell sorters; or particle sizers). In some cases, where the substrate is in the form of particles or beads, detection of eggs can be indirect by detection of the beads/particles themselves. Beads/particles used for this purpose can optionally be labeled with suitable chromophores or fluorophores to facilitate detection. It is understood that for the purposes of this document, the phrase "detection reagent" encompasses all of the constituents required to achieve detection. For example, a detection agent consisting of an antibody bound to an enzyme also by definition further comprises the appropriate enzyme substrates, buffers and other agents required to effect the color change required for the detection.

Detection can be achieved with eggs still bound to the solid substrate, or following release of the eggs from the substrate, and binding of detection reagents can be achieved either before or after capture. In some cases, detection can be facilitated by treating the eggs with chemicals to either expose or release components that can be detected. Non-limiting examples of such chemicals include surfactants, oxidizing agents, chaotropic agents and enzymes.

By selection of the appropriate capture and detection reagents, egg counting can be tuned to detect either all eggs in the sample or eggs of various taxonomic groups from entire phyla down to the species level. This may be achieved by using single reagent for capture and detection, or by using multiple reagents in either or both the capture and detection steps. By separating eggs from different classes/species, and in conjunction with the appropriate reagents, the abundance of numerous classes or species of parasite eggs can be resolved in a single test.

Capture of eggs can also be facilitated by inducing aggregation of eggs in solution by the addition of multivalent molecules capable of binding to the eggs. Flocculated eggs can either be bound directly to the substrate from the fecal suspension or following isolation by physical techniques such as centrifugation or flotation.

Capture and detection can also be conducted simultaneously, for example by detecting voltage changes upon eggs binding to egg-specific antibodies that have been attached to a carbon-nanofiber network, or by optical methods such as surface plasmon resonance or refraction.

In one case detection could be achieved without capture of the eggs where binding of egg-specific molecules, such as antibodies or lectins, labeled with fluorophores is detected by changes in fluorophore anisotropy or polarization.

Thus, in some aspects, this disclosure provides novel methods for detecting the presence or absence of chitin-containing parasitic helminth eggs or protozoan oocysts from environmental samples (e.g., fecal samples). The methods disclosed herein provide methods which can be performed both rapidly and on-site. More importantly, the methods disclosed herein are capable of detecting helminth eggs from each of the major taxa of parasitic helminths (e.g., cestodes, nematodes, trematodes and monogeneans) in a rapid, cost-efficient manner. Common genera of helminth parasites infecting animals include, for example, *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Pearsonema, Heterakis, Toxocara, Ascardia, Oxyuris, Ancyclostoma, Uncinaria, Toxascaris* and *Parascaris Ancylostoma, Necator, Trichinella, Capillaria, Dioctophyme, Eimeria, Coccidia, Bursaphelenchus, Ostertagia, Mecistocirrus, Trychostrongylus, Trichuris, Bunostoinuin, Oesophagostomurn, Chabertia, Chabertia, Ancylostoma, Paragonimus, Baylisascaris, Aphelenchoides, Meliodogyne, Heterodera, Globodera, Nacobbus, Pratylenchus, Ditylenchus, Xiphinema, Longidorus, Trichodorus, Nematodirus* and *Enterobius*.

The methods of the invention may be used for human and/or veterinary usage as well as in the area of environmental testing.

In one aspect, the method of the invention provides for obtaining a biological sample comprising a fecal sample (e.g. a stool sample) from a mammalian subject (e.g., an animal or human subject). For example, the fecal sample can be a mammalian fecal sample obtained from a horse, cow, pig, goat, sheep, llama, deer, dog, cat, bird or human. By "obtaining" is meant collecting, purchasing, or otherwise acquiring the fecal sample.

In some aspects, the novel methods disclosed herein comprise contacting a sample suspected of containing helminth eggs or protozoan oocysts with a GlcNAc binding domain or fragment thereof. The term "N-acetyl-D-glucosamine (GlcNac) binding domain" as used herein refers to any molecule including natural or genetically modified N-acetyl-D-glucosamine (GlcNac) binding proteins, inorganic molecules, and organic molecules having a specific binding affinity for N-acetyl-D-glucosamine, including any fragments, derivatives or analogs thereof.

The term "N-acetyl-D-glucosamine (GlcNac) binding protein" as used herein refers to any molecule including natural or genetically modified proteins, peptides, or antibodies having a specific binding affinity for N-acetyl-D-glucosamine, including any fragments, derivatives or analogs thereof. Exemplary GlcNac binding proteins include, for example, lectins, chitinases, chitin binding proteins, or a chitin binding domains (CBD).

In some aspects, the novel methods disclosed herein comprise contacting a sample suspected of containing helminth eggs or protozoan oocysts with a chitin binding protein or fragment thereof. The term "chitin binding protein" as used herein refers to any molecule including natural or genetically modified proteins, peptides, antibodies, or having a specific binding affinity for chitin. Chitin binding proteins include, for example N-acetyl-D-glucosamine (GlcNac) binding proteins, chitinases, and protein chitin binding domains (CBD).

The term "lectin" as used herein refers to any molecules including proteins, natural or genetically modified, that interact specifically with saccharides (i.e. carbohydrates). While the examples herein refer to a natural plant lectin, the term "lectin" herein refers to lectins from any species, including but not limited to plants, animals, insects and microorganisms, having a desired carbohydrate binding specificity. Examples of plant lectins include, but are not limited to, the Leguminosae lectin family, such as ConA, soybean agglutinin, and lentil lectin. Other examples of plant lectins are the Gramineae and Solanaceae families of lectins. Examples of animal lectins include, but are not limited to, any known lectin of the major groups S-type lectins, C-type lectins, P-type lectins, and I-type lectins.

In some embodiments, the lectin is selected from the group consisting of wheat germ agglutinin (WGA), soybean agglutinin (SBA), *Maclura pomifera* lectin (MPL), *Bauhinia purpurea* lectin (BPL), *Datura stramonium* lectin (DSL), *Lycopersicon esculentum* lectin (LEL), *Solanum tuberosum* lectin (STL) and *Psophocarpus tetragonolobus*-II (PTL-II).

The term "chitin-binding domain" or "CBD" as used herein refers to any refers to any molecules including proteins, natural or genetically modified, that interact specifically with chitin. CBD are known to the person skilled in the art and can be derived from chitinases or from cuticular proteins from arthropods, and commercially available from multiple sources, including the IMPACT™ kit supplied by New England Biolabs.

The term "chitinase" generally describes an enzyme specific for the substrate chitin. Many different types of chitinases occur naturally. For example, chitinases are found in microbes such as *Serratia, Vibrio,* and *Streptomyces*.

The disclosure provides a N-acetyl-D-glucosamine binding domains, including N-acetyl-D-glucosamine binding proteins, conjugated to one or more detectable moieties. As used herein, the terms "label" and "detectable moiety" are interchangeable and shall refer to moieties that can be attached to (e.g., conjugated to) a binding protein to thereby render the binding protein detectable by an instrument or method.

Non-limiting examples of detectable moieties suitable for use in the practice of the disclosed invention include, for example, a hapten, an enzyme, a chromophore, an antibody epitope, an antigen, a fluorophore, a radioisotope, a nanoparticle, a member of an binding pair, a luminescent compound and a metal chelate.

As used herein, the terms "fluorescence label" and "fluorophore" used interchangeably and refer to any substance that emits electromagnetic energy at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals.

Representative fluorophores for use in the methods provided herein include, for example, green fluorescent protein, blue fluorescent protein, red fluorescent protein, fluorescein, fluorescein 5-isothiocyanate (FITC), cyanine dyes (Cy3, Cy3.5, Cy5, Cy5.5, Cy7), Bodipy dyes (Invitrogen) and/or Alexa Fluor dyes (Invitrogen), dansyl, Dansyl Chloride (DNS-Cl), 5-(iodoacetamida)fluorescein (5-IAF, 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, rhodamine dyes (5-carboxyrhodamine 6G hydrochloride, Lissamine rhodamine B sulfonyl chloride, rhodamine-B-isothiocyanate (RITC (rhodamine-B-isothiocyanate), rhodamine 800); tetramethylrhodamine 5-(and 6-)isothiocyanate (TRITC)), Texas Red™, sulfonyl chloride, naphthalamine sulfonic acids including but not limited to 1-anilinonaphthalene-8-sulfonic acid (ANS) and 6-(p-toluidinyl)naphthalen-e-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, Naphtyl Styryl, 3,3'dipropylthiadicarbocyanine (diS-C3-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, IR-125, Thiazole Orange, Azure B, Nile Blue, Al Phthalocyanine, Oxaxine 1,4',6-diamidino-2-phenylindole. (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofiuors, Coronene, and metal-ligand complexes.

Haptens for use in the methods provided herein include, for example, digoxigenin, glutathione and biotin.

Enzymes for use in the methods provided herein include, for example, alkaline phosphatase (AP), beta-galactosidase, horse radish peroxidase (HRP), soy bean peroxidase (SBP), urease, beta-lactamase and glucose oxidase.

In some embodiments, the GlcNac binding protein is an antibody. Anti-chitin (e.g., anti-GlcNac) antibodies have been disclosed in U.S. Pat. No. 5,004,699, those antibodies can be used for the detection of fungi and yeasts (U.S. Pat. No. 5,004,699).

The detectable moiety can be a specific member (a first member or a second member) of a binding pair. Binding pairs for use in the methods provided herein include, for example, biotin/streptavidin, biotin/avidin, biotin/neutravidin, biotin/captavidin, epitope/antibody, protein A/immunoglobulin, protein G/immunoglobulin, protein L/immunoglobulin, GST/glutathione, His-tag/Metal (e.g., nickel, cobalt or copper), antigen/antibody, FLAG/M1 antibody, maltose binding protein/maltose, calmodulin binding protein/calmodulin, enzyme-enzyme substrate, and receptor-ligand binding pairs. In some embodiments, the GlcNac binding protein is conjugated to a first member of binding pair (e.g., biotin, avidin, neutravidn, captavid, antibody, antigen, protein A, protein G, protein L, GST, His-Tag, FLAG, MBP, calmodulin binding protein, an enzyme, a receptor or ligand).

In one embodiment, the GlcNac binding protein is wheat germ agglutinin and the detectable moiety is fluorescein. In another embodiment, the GlcNAc binding protein is a protein containing a chitin binding domain and the detectable moiety is fluorescein.

In some aspects, the methods provided herein employ a dye that binds directly to chitin and fluoresces when exposed to a fluorescence-exciting light, such as the dyes disclosed in U.S. Pat. No. 6,440,388. Non-limiting examples of dyes that bind or conjugate chitin and fluoresce in ultraviolet or visible light include calcofluor white, Uvitex 3B (distyryl biphenyl fluorescent whitening agent), Rylux BA, Rylux BSU (1,4-benzenedisulfonic acid-2,2'-[ethyleneidylbis[(3-sulpho-4,1-phenylene)imino[6-bis(2-hydroxyethyl)amino]-1,3,5-trihexasodium salt) (Ostacolor, Pardubice, Czech Republic) and Blankophor (disodium 4,4'-bis {(4-anilino)-6-morpholino-1,3,5-triazin-2-yl)amino}stilbene-2,2'-disulphonate).

In some embodiments, a first member of a binding pair is conjugated to a GlcNac binding protein and the second member of the binding pair is immobilized to a solid support. In other embodiments, a first member of a binding pair is conjugated to a GlcNac binding protein and the second member of the binding pair is conjugated to an enzyme, an antibody epitope, an antigen, a fluorophore, a radioisotope, a nanoparticle, a member of a second binding pair, and a metal chelate. For example, the first member of the binding pair can be biotin and the second member of the binding pair can be streptavidin, avidin, neutravidin or capravidin, and the second member of the binding pair conjugated to an enzyme (e.g., alkaline phosphatase (AP), beta-galactosidase, horse radish peroxidase (HRP), urease, soy bean peroxidase (SBP), beta-lactamase or glucose oxidase).

In some cases, the chitin (e.g., GlcNac) may be partially or totally blocked off by a polysaccharide capsule or other type of macromolecular coating found in helminth eggs. However, chitin is extremely robust, hence, enzymatic digestions using proteases or polysaccharides such as a glucanase or mannase can be used to permeate or remove the blocking layer before chitin detection. Alternatively, extreme treatment such as bleaching in a bleach solution (1% NaOCl, 0.5 M NaOH, or similar composition with higher or lower concentrations of individual chemical), as described in US2007/0099234) can be used to remove the masking layer. Thus, in some embodiments, the methods provided herein further comprise, prior to contacting the helminth eggs with a GlcNac binding protein, a step of treating the sample with a bleach or other shell-exposing solution.

According to the methods provided herein, parasite eggs can be detected in a suspension of in a suspension of animal feces in water or other suitable liquid (including buffered solutions) by a two-step process; egg capture and egg detection.

In some aspects, the methods described herein comprise capturing eggs by filtration, the methods comprising providing a fecal solution comprising a fecal sample suspended in a sample buffer, flowing the fecal solution through a first filtration membrane to form a first filtrate, and flowing the first filtrate through a second filtration membrane to capturing the helminth eggs on the second filtration membrane.

In one aspect, the methods comprise obtaining a fecal solution comprising a fecal sample suspended in a sample buffer, flowing the fecal solution through a first filtration membrane to form first filtrate, and flowing the first filtrate through a second filtration membrane, wherein helminth eggs are captured on the second filtration membrane. The methods further comprise contacting the helminth eggs captured on the second filtration membrane with a GlcNac binding protein conjugated to a detectable moiety and detecting the presence or absence of helminth eggs in the fecal sample based on the signal intensity detectable moiety.

In one aspect, the methods provided herein comprise flowing the fecal solution through a first filtration membrane (e.g., a filter). Flowing the fecal solution through a first filtration membrane allows for separation of eggs from fecal particles. Thus, the first filtration membrane comprises a pore size which allows for eggs to pass freely through the filter (e.g., having a pore size of at least 80 microns) and also captures fecal particles.

Thus, the methods provided herein comprise the use of a first filtration apparatus. The pore size the first filtration apparatus is generally selected such that the pores are large enough allow helminth eggs and protozoan oocyts to freely pass through, while being small enough to capture fine particles (e.g., less than about 450 microns, less than about 425 microns, or less than about 400 microns) from the fecal solution. In some embodiments, the first filtration membrane of the first filtration apparatus comprises a pore size of between about 85 microns and about 350 microns, between about 100 microns and about 300 microns, between about 125 microns and about 250 microns, between about 150 microns and about 200 microns, or about 85 microns, about 90 microns, about 95 microns, about 100 microns, about 120 microns, about 125 microns, about 150 microns, about 175 microns, about 200 microns, about 250 microns, about 300 microns, about 350 microns, or, at most, about 400 microns.

In one aspect, the methods provided herein comprise flowing the fecal solution through a second filtration membrane (e.g., a filter). Thus, the second filtration membrane comprises a pore size which allows fluid to pass freely through the filter and also captures eggs or oocyts (e.g., having a pore size of at 80 microns or less).

Thus, the methods provided herein comprise the use of a second filtration apparatus. The pore size the second filtration apparatus is generally selected such that the pores are large enough allow fluid and fine particles to freely pass through, while being sized (i.e., being small enough) to capture helminth eggs from the fecal solution. The characteristic size and diameter of parasitic helminth eggs is between about 20 microns and 80 microns. Thus, to capture helminth eggs from the fecal solution, the second filtration membrane of the second filtration apparatus comprises a pore size of between 5 and about 45 microns, between 10 and about 45 microns, between 15 and about 45 microns, between about 20 microns and about 45 microns, between about 25 microns and about 40 microns, between about 30 microns and about 35 microns, or about 5 microns, about 10 microns, about 15 microns about 20 microns, about 25 microns, about 30 microns, about 35 microns, about 40 microns, or about 45 microns. Since many protozoan oocyts are smaller than helminth eggs, smaller pore filters can also be used e.g. between about 0.1 and about 10 microns or between about 5 and about 20 microns.

Minimization of extraneous fecal debris in the fecal sample is beneficial for consistent fecal egg counts and, typically, large particles and debris have to be filtered out of the fecal sample before the fecal sample is suitable for contact with a GlcNac binding protein. Thus, the methods disclosed herein optionally comprise the use of a bulk filtration apparatus to remove larger particles and debris. The pore size the bulk filtration apparatus is generally selected such that the pores are large enough allow helminth eggs and proteozoan oocyts to freely pass through, while being small enough to capturing large particles (e.g., particles greater than or equal to 400 microns) and debris from the fecal material. For example, the filtration membrane of the bulk filtration apparatus comprises a pore size of between about 400 microns and about 800 microns, between about 425 microns and about 750 microns, between about 450 microns and about 700 microns, between about 500 microns and about 650, or between about 550 microns and about 600 microns. In some embodiments, the bulk filtration apparatus may be connected directly to the vessel used to collect the fecal sample (e.g., the collection vessel). In some embodiments, the bulk filtration membrane has a pore size of between about 400 microns and about 450 microns, the first filtration membrane has a pore size of between about 85 microns and about 120 microns, and the second filtration membrane has a pore size of between about 20 microns and about 30 microns.

As can be appreciated in the art, there are many ways to flow volume of liquid (e.g., a solution) through a filtration membrane, such as gravity flow, pressure or with the aid of a pump.

The methods of the present invention allow for the visualization of chitin-containing parasitic helminth eggs and protozoan oocyts by labeling chitin with a suitable reporter (e.g., a detectable moiety). Following chitin binding by a suitable reporter (e.g., a detectable moiety), the quantitation of eggs could be accomplished visually (1) by comparison to a color chart, by using an inexpensive single-wavelength colorimeter or fluorimeter, or by digitally quantifying the color following photography using a camera, cell phone, tablet or other digital imaging device, or (2) in the case of a fluorescent chitin-binding derivative, by imaging the sample under appropriate illumination with either a cell-phone or other camera fitted with appropriate optics in conjunction with automated image analysis.

The detectable moiety may be illuminated with a wavelength of light that results in a detectable optical response, and observed with a means for detecting the optical response. Upon illumination, such as by an ultraviolet or visible wavelength, the fluorescent compounds, including those bound to the GlcNac binding protein or to a specific binding pair member, display intense visible absorption as well as fluorescence emission. Selected equipment that is useful for illuminating the fluorescent compounds of the invention includes, but is not limited to, advantageously, equipment useful for illuminating the fluorescent compounds include portable lamps (e.g., hand-held ultraviolet lamps). These illumination sources are optionally integrated into portable laser scanners, fluorescence microplate readers, fluorescent gel imagers, standard or mini fluorometers, standard or mini colorimeters or chromatographic detectors. Prior to detection, excess excitation light is reduced or removed by passage through an optical filter that prevents some or all of the excitation wavelengths from passing while allowing some or all of the fluorescent emission wavelengths to pass. This fluorescence emission is optionally detected by visual inspection, or by use of any of the following imaging devices: a digital camera, a mobile phone, a smartphone, a tablet, a portable computer, a computer, and a scanner.

The invention also provides kits for detecting the presence or absence of helminth eggs and protozoan oocyts in fecal samples. The kits of the invention can take on a variety of forms. Typically, the kits will include reagents suitable for detecting helminth eggs in a sample. Optionally the kits may contain one or more control samples.

The kits of the present invention optionally comprise a collection vessel in which an amount of a fecal sample can be placed and diluted by a suitable buffer solution. The vessel can then be sealed and the fecal sample and buffer shaken or homogenized to produce a uniformly mixed fecal solution. The buffer solution may be plain tap water or appropriate buffered or flotation media. The collection vessel can be a disposable vessel for fecal collection or a reusable vessel.

The collection vessel may be for example in the form of a regular capped tube, having graduations, which indicate the volume of the raw stool specimen which is to be placed inside the tube, as well as the amount of the diluting liquid to be added.

In some embodiments, the collection vessel is attached to a bulk filtration apparatus.

The kit may also comprise a construction for collecting the fecal sample, such as a disposable vessel for stool collection, etc., as well as a scooping device, for example in the shape of a small spoon to pick a determined amount of fecal material. The scooping device (scoop) may be an integral part of the vessel's cap.

In some embodiments, the kits of the invention comprise a first filtration apparatus, optionally a second filtration apparatus, and optionally a bulk filtration apparatus as described herein.

The kits of the present invention comprise a reagent (e.g., a reagent solution) containing a GlcNAc binding protein. The GlcNac binding protein can be a lectin or CBD as described herein. Optionally, the GlcNac binding protein is conjugated to a detectable moiety. In one embodiment, reagent contains a dye capable of directly binding or conjugating to chitin and emit fluorescence upon exposure to light, and a source of light that emits a wavelength capable of exciting fluorescence from the chitin bound dye.

The kits can include a portable system for detecting the detectable moiety, such as a fluorometer, a colorimeter, a spectrophotometer, or other imaging device. The kits may also include a cradle designed for holding the sample and the portable system for detecting the detectable moiety. In some embodiments, the kit comprises a cradle that holds or contains an imaging device.

Some aspects of the kits (for example the detection apparatus or reusable parts of a filtration system) can be sold separately to other aspects of the kits (for example the detection reagents of single-use filter modules).

The kits of the invention may be used for human and/or veterinary usage.

The general principles outlined above can be used to design a large number of systems for detecting the presence and abundance of parasite eggs in fecal suspensions. For the purposes of illustration there follows a number of non-limiting examples of several egg counting assays that can be produced using these principals. These examples are merely provided for the purposes of illustration of some of the many different modes in which the invention can be practiced and should not be considered as descriptive of the entire invention.

It should be noted that successful detection and quantification of parasite eggs requires both a method to separating (and ideally concentrating) eggs from the bulk of the fecal sample, and then a method for detecting said eggs. If the separation method also results in the possible co-isolation of other fecal components and the detection method does not discriminate between them, then the assay will not be specific. For example, Zhang and McReynolds23 disclose the use of the chitin binding domain (CBD) from various chitinase enzymes for the detection of chitin in biological samples for the purposes of diagnosis. However since many organisms, for example, yeast, other fungi, nematodes (and their eggs) all contain chitin, its mere detection cannot be regarded as conclusively diagnostic of any of these organisms. Similarly, Winters[24] discloses the use of anti-chitin antibodies to detect chitin in biological samples as a method for diagnosing the presence of yeast and fungi. Winters does not, however, anticipate the possibility of detection of chitin in helminths or their eggs, and so the assay disclosed cannot be considered specific for either yeast and fungi nor for helminths or their eggs unless the possibility of the presence of one of these groups can be eliminated. In the case of animals feces (and particularly for herbivores) the presence of both yeast and fungal cells (and spores) and of insect fragments is possible and so the presence of chitin alone cannot be considered definitively diagnostic of the presence of parasite eggs, nor can the quantification of parasite eggs be considered reliable in the presence of a potentially varying background other chitin-containing organisms.

It has also been suggested that various lectins can be used to distinguish between different species of parasite and their eggs. However, most lectins are well known to be semi-specific since they recognize sugar structures that could be present in a diverse array of organisms. Thus, while lectin binding could distinguish between reactive and non-reactive species, as a general principal, lectin binding alone cannot provide a conclusive diagnosis of parasite infestation unless all other possible contaminating organisms have been shown to be binding-negative.

In some embodiments, a fecal sample is suspended in water or a suitable buffer such as, but not limited to, phosphate buffer saline (PBS) and contacted with beads coated with a reagent capable binding to parasite eggs (e.g., a GlcNac binding protein). The reagent can be specific to such eggs only, or to eggs of taxonomic groups of interest, or specific to both eggs and other components of the feces. Specific reagents include, for example, monoclonal antibodies raised to a particular organism of interest or that recognizes multiple taxa of organisms, or a polyclonal antibody raised against multiple taxa or single organisms, or mixtures of multiple monoclonal and/or polyclonal antibodies. Non-specific reagents include proteins such as CBD or lectins or mixtures thereof, either alone or in combination with antibodies. In the case of CBD, binding can be enhanced by applying CBD in at elevated pH above 7 and/or at high salt concentration, for example, but not limited to 0.5M NaCl. For the purposes of this document, CBD is understood to refer to not only a single chitin binding domain from any species, but also to multiple CBDs produced by either chemical conjugation or by expression of genetically fused of tandem repeats of two more CBDs with or without intervening non-CBD sequences. In is also understood that CBD need not be a natural sequence found in nature but also an artificial peptide sequence capable of binding chitin, or mutant variants of CBD with either the same or differing binding affinities compared to the natural sequences.

In another embodiment, the buffer also may optionally contain reagents to help to expose the desired target binding sites on the eggs and include, but are not limited to, surfactants (such as Tween-20, sodium dodecyl sulfate and Triton X-100), oxidizing agents (such as sodium hypochlorite, N-chlorotosylamide or hydrogen peroxide), chaotropes (such as urea or guanidinium hydrochloride), enzymes (such as proteases, glycosidases or lipases) or bleach.

Upon binding, beads loaded with eggs (and possibly other fecal components) are physically separated from the remainder of the feces by, for example, filtration (using a filter with pore sizes sufficient to retain the beads and their cargo, but not other fecal debris), or by centrifugation. Alternatively, the beads could be imbedded with iron, and such paramagnetic or magnetic beads (which are readily available commercially) could be separated from the remainder of the fecal suspension by application of a magnetic field.

Upon bead isolation, beads are suspended in a small volume (for example 100 μl) of buffer and examined optically using a microscope. While this method does not remove the inconvenience of visual inspection, it does allow the isolation and counting of large numbers of eggs from feces. Current methods sample only 1/25 to 1/200 of a several gram fecal sample, resulting in a low sensitivity and high variability. This method eliminates both of these problems by eliminating such subsampling.

Figure 1:
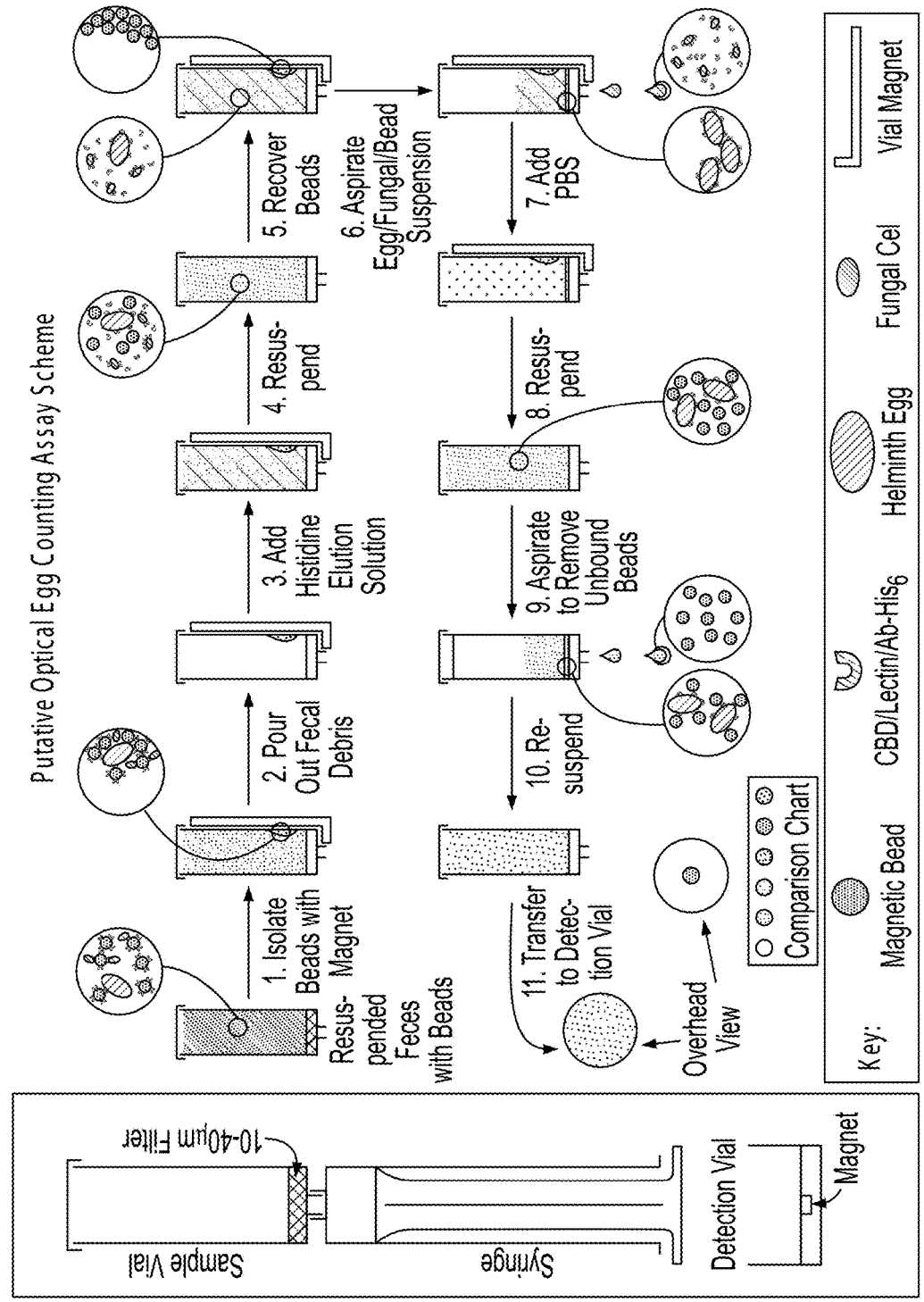
FIG. 1 is a schematic diagram showing a method according to the invention for detecting the presence or absence of helminth eggs in a fecal sample using magnetic beads for egg capture.

In one aspect, which is depicted in FIG. 1, eggs are isolated as described in Example 1 using magnetic beads. In one embodiment the capture reagent that is attached to the beads is CBD which is reversibly attached to the magnetic bead by means of sequence of 6 histidine residues at its N- or C-terminus which bind to nickel atoms on the surface of the beads. In another embodiment, the CBD is fused to a carrier such maltose binding protein (MBP) which is used to reversibly attach the CBD to beads coated with maltose. In these embodiments, CBD can be detached from the beads by the addition of either histidine, imidazole or maltose as non-limiting examples.

Upon isolation of eggs and removal of fecal debris, bound material is released from the beads by the addition of the appropriate elution agent (for example, a solution of histidine (or imidazole) or maltose). Beads are then reattached to the magnet and the solution containing the freed eggs and fecal material drawn though a filter. The purpose of this step is to separate fungal and yeast cells, which could also bind to CBD, from the eggs. The filter pore size is selected to allow smaller (5-40 μm) yeast and fungal cells to pass through, while retaining the larger egg cells (50-100 μm), thereby providing the specificity that CBD alone does not provide in such a system. Upon aspiration of the solution, only eggs (with attached CBD) and beads (which are adhered to the side of the tube by the magnet) are retained in the testing chamber.

Since aspiration of the solution removes the elution molecule (e.g. histidine (or imidazole) or maltose), addition of fresh buffer and removal of the magnet allow the eggs to rebind the beads via the attached CBDs. Since the beads are brown-colored due to their iron content they themselves can be used to quantify the number of eggs present after removal of beads that are not bound to eggs. Since the beads are themselves much smaller than the eggs (commercially available beads range in size between 0.2 and 5 microns) unbound beads are removed by a second passage through the same filter (though a different tube and fresh filter could also be used).

Retained, egg-bound beads are then resuspended in fresh buffer and quantified by pouring the suspension into a detection chamber. The base of the chamber contains a small magnet that attracts the egg-beads complexes into a small surface area. The purpose of this detection chamber is to concentrate the egg/bead complexes to intensify the bead color and allow the visual determination of the color intensity in comparison to a standardized color chart in order to quantify the number of beads (and therefore eggs) present in the sample. Alternatively the area can be imaged by an optical sensor to obtain a more accurate reading of color intensity.

The number of beads (and therefore eggs) is determined optically using either a spectrophotometer or a single-wavelength colorimeter to measure the turbidity of the egg/bead suspension.

In some embodiments, the eggs are quantified upon initial release from the beads by measuring their ability to scatter light. Yeast and fungi, if present, can be differentiated from eggs based on their smaller size by selection of the appropriate wavelength of light for detection, or by using a particle sizer.

In other embodiments, the capture reagent need not be CBD and could, by way of non-limiting example, be an antibody (mono- or polyclonal) or a lectin (or mixture of lectins).

In another embodiment, the capture reagent is specific only to parasite eggs, or to only a subset of eggs of clinical interest, then either only one aspiration step (with no elution reagent) could be used to remove unbound beads and then facilitate quantification of egg/bead complexes as described above.

In yet another embodiment, if the capture reagent also binds to yeast and/or fungi and if yeast and/or fungal cells bound to the beads do not form aggregates or complexes large enough to be retained by the filter (whose pore size is small enough to retain egg/bead aggregates/complexes), or if yeast and/or fungal burden does not produce a clinically meaningful background in the assay, then either only one aspiration step (with no elution reagent) could be used to remove unbound beads and yeast/fungi (if present) and then facilitate quantification of egg/bead complexes as described above.

In another embodiment, detection of bound eggs is achieved by a chromogenic reaction utilizing, by way of non-limiting examples, protein assays, carbohydrate assays, or by attachment of other recognitions molecules such as antibodies, lectins or CBD to the eggs. In the latter case, the molecules are conjugated to reporter groups such as chromophores, fluorophores, colored microbeads, quantum dots, colloidal metals or chromogenic enzymes (e.g., HRP or AP).

In another embodiment, and in the case of egg-specific capture, detection can occur immediately after egg capture and washing of the beads suing methods such as those detailed elsewhere and requires no filtration steps.

In another embodiment, in the case of egg-specific capture detection of eggs can be carried out either with or without release from the beads using particle counting devices such as a coulter counter a cell sorter or particle sizer.

In yet another embodiment of the invention, the egg/bead complexes are treated with reagents to release components for chemical detection. Such reagents include, but are not limited to, proteases, glycosidases (including chitinase), surfactants, chaotropes and oxidizing agents.

The methods disclosed herein allows for the quantification of fecal egg burdens by veterinarians on site, or by animal owners themselves, since there is no requirement for expensive, specialized equipment or training (magnets, beads, single-wavelength colorimeters can all be manufactured inexpensively and require no specialized training to operate).

In one aspect, the methods disclosed herein comprise the use of capture reagents (such as an antibody, lectin or CBD) bound to a solid surface such as a two dimensional strip of material, though the actual shape may be varied as necessary. The strip can consist of any compatible material including, but not limited to, a plastic (such as polyethylene, polypropylene or polystyrene) or other polymer (such as cellulose, phosphocellulose or polyvinylidene difluoride). The capture reagent is bound to the surface by one of many reactive chemistries available to one skilled in the art and dependent on the nature of surface chemistry. Possible, non-limiting molecules capable of binding proteins to such surfaces include disuccinimidyl suberate, dimethyl adipimidate, succinimidyl-4-(N-maleimidomethyl)cyclohexane-1-carboxylate or N-hydroxysuccinimide. The capture reagent need not be applied to the whole of the surface and can be localized to a particular area such as a spot or strip.

In another embodiment, the capture reagents are attached to the surface reversibly in a manner described above.

The surface is then contacted with the fecal suspension to allow the eggs to bind and then washed to remove fecal contaminants. The strip is then contacted with a solution containing detection reagent. The detection reagent can again be any number of molecules capable of binding to the eggs, including antibodies, lectins or CBD, conjugated to a suitable reporter. Reporters need to be capable of generating a visible signal on the surface and include chromophores, fluorophores, enzymes, colloidal metals, quantum dots, or colored microparticles. In the case of enzymes, the surface is washed and then contacted with a suitable substrate, whose product needs to be insoluble in order to be deposited onto the surface for visualization. Two non-limiting examples of such a system are the enzyme horse radish peroxidase and the substrates 4-chloro-1-naphthol or 3,3'-diaminobenzidine, or the enzyme alkaline phosphatase and the substrates 5-bromo-4-chloro-3-indolyl phosphate and nitroblue tetrazolium.

Upon deposition of color, which is proportional to the number of eggs captured on the substrate, the number of eggs is quantitate either by visual comparison to a calibrated color chart or by using a device such as a colorimeter or densitometer.

In another embodiment of the invention, enzymatic detection of immobilized eggs occurs with substrates whose soluble colored products are released into the solution to produce a color change than can be detected optically.

In another embodiment of the invention, and in the case where the capture reagent is bound reversibly to the surface, the eggs/capture reagent are released after binding and washing and then detected in solution.

As in other embodiments, the eggs can optionally be treated at any stage by reagents already disclosed above to expose sites or release detection molecules necessary for either capture or detection.

In some aspects, the methods disclosed herein are adapted into a lateral flow format similar to that used in, for example, consumer home pregnancy tests. One end of the device containing a sample chamber is placed into the solution, or samples of the solution are dispensed into a chamber in the device. The chamber contains a detection agent such as, but not limited to, an antibody, lectin or CBD conjugated to a detection agent such as colored microparticles, quantum dots or colloidal metals.

Upon entry the chamber the sample (including eggs now bound to detection reagents) are wicked up a strip of solid substrate such as paper or other sintered polymer by means of capillary action. A portion of this strip is coated with a capture reagent similar to those described above, allowing for the immobilization the eggs and the associated colored detection reagent.

Development of color on the region of strip coated with capture reagent by the adherence of egg/reagent complexes is diagnostic of the number of eggs present in the feces. The number can be determined visually by comparison to a calibrated color chart, or electronically by imaging the color with a charge coupled device or similar device followed by appropriate signal processing.

To maximize the capture of eggs, ideally the capture reagent is most specific for eggs, while the detection reagent can be less discriminatory, though the converse can also be true. As in other embodiments described elsewhere, the major criterion for the capture and detection reagents is that binding to both of them is mutually exclusive for all fecal constituents except parasite eggs or subsets of parasite eggs.

As in other embodiments, the eggs can optionally be treated in the fecal suspension by reagents already disclosed above to expose sites or release molecules necessary for either capture or detection.

In some embodiments, the strip contains two or more areas coated with capture agents that are each specific to different species taxonomic groups. In this case numerous colored areas develop that correspond to the quantity of different kinds of parasite eggs.

In another embodiment, the sample chamber contains multiple detection agents that each recognize eggs from different species or taxonomic groups. Labelled eggs are then captured in a single area and the amount of each type of egg determined by imaging the area and then computationally reconstructing the relative contribution of each colored reagent (and therefore egg type/number) to the final color detected.

The detection reagents can be mixed directly with the fecal suspension prior to application of or to the device, and thus are not stored in the device's sample chamber.

As in other embodiments, the eggs can optionally be treated at any stage by reagents already disclosed above to expose sites or release molecules necessary for either capture or detection.

In some aspects, the methods comprise capturing eggs with a suitable capture reagent that is itself immobilized on a transparent surface using methods described above. The transparent surface can take the form of any container including, but not limited to, a tube, cuvette, a dish or a plate containing one or more wells.

Upon washing to remove fecal debris, detection reagent is added that is labelled in a manner or manners that are described above. The color of the bound detection reagent (or the color developed by the enzymatic activity of the detection reagent) is measured either visually and compared to a calibrated color chart, or by using a device such as a colorimeter, microplate reader, spectrophotometer or fluorometer.

In another aspect of the invention, there is no detection reagent and the binding of eggs is determined by measuring a change in the refractive index of the clear surface upon egg binding, or by other optical methods such as surface plasmon resonance or refractometry.

As in other embodiments, the eggs can optionally be treated at any stage by reagents already disclosed above to expose sites or release molecules necessary for either capture or detection.

Figure 2:
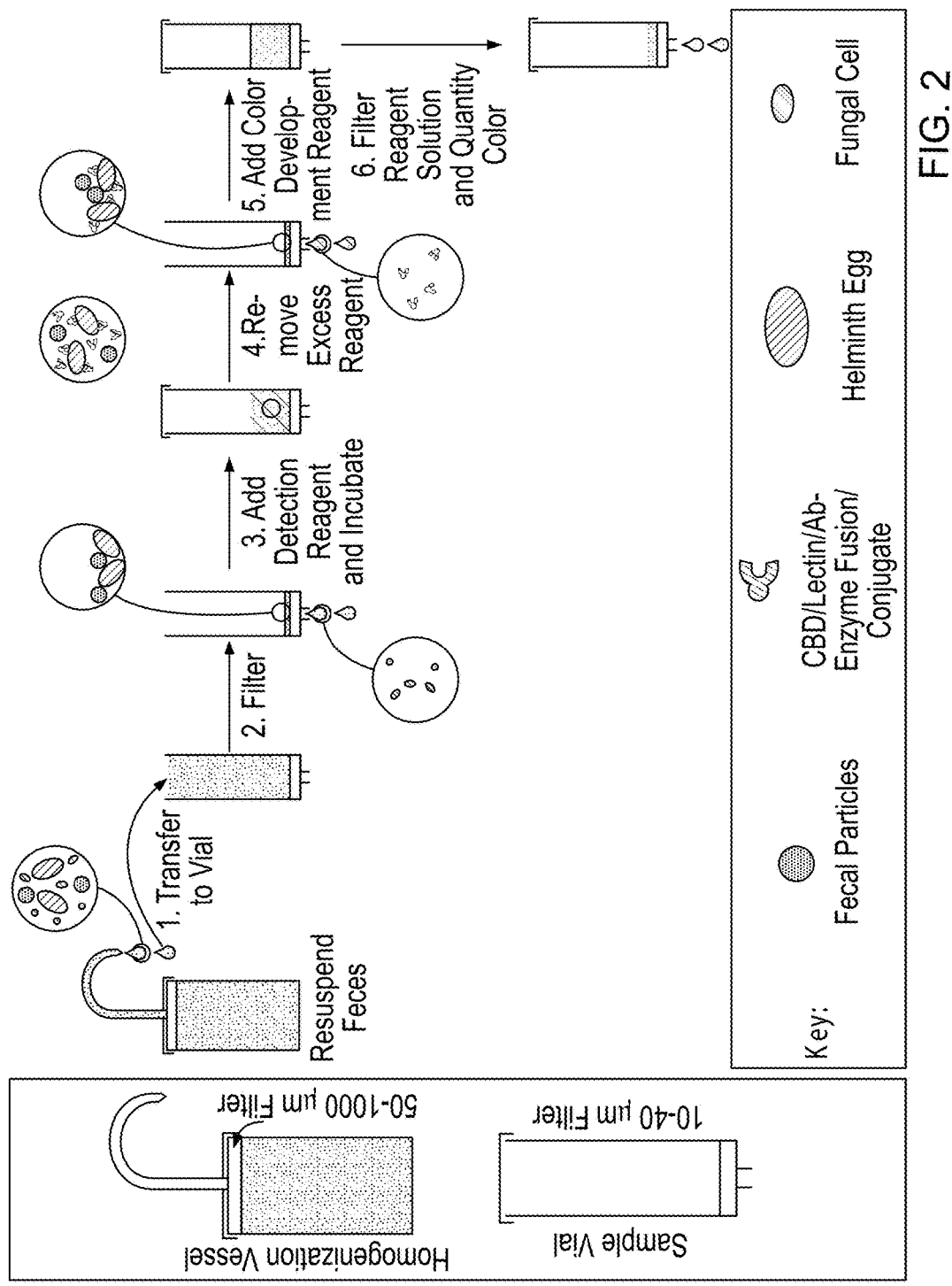
FIG. 2 is a schematic diagram showing a method according to the invention for detecting the presence or absence of helminth eggs in a fecal sample using a multistep filtration process.
Figure 3A:
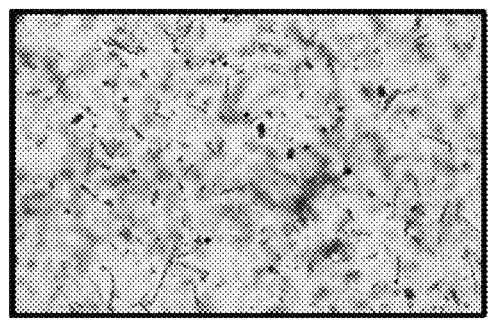
FIG. 3A to 3D are photographs showing samples before and after bleaching (panel A=unbleached; panel B=sample following bleaching for 4 minutes; panel C=sample following bleaching for 6 minutes; and panel D=sample following bleaching for 8 minutes)
Figure 3B:
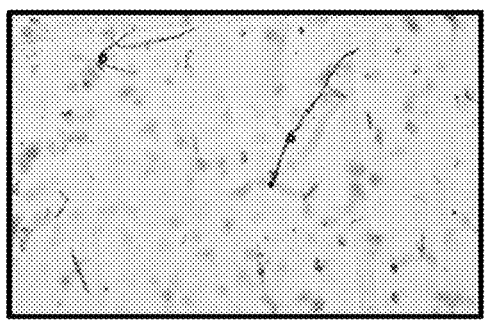
Figure 3C:
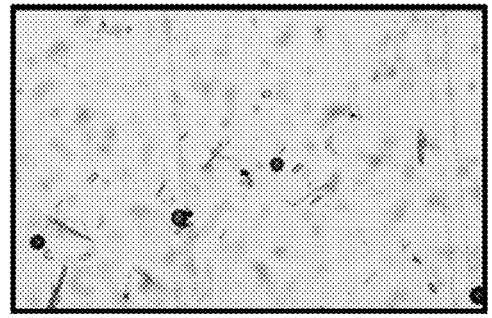
Figure 3D:
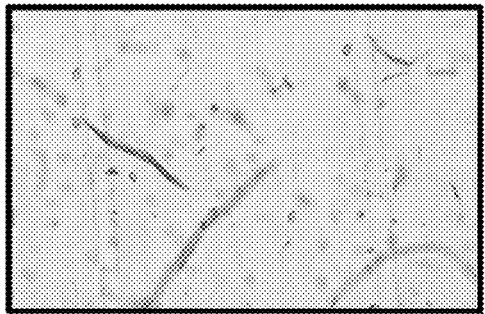

In this embodiment, and example of which is depicted in FIG. 2 for the purposes of illustration, eggs are captured and separated from yeast and fungi using a physical method—namely filtration. Eggs are homogenized in a suitable vessel and then passed through a first filtration membrane having a pore size to facilitate the passage of eggs (e.g., between about 85 microns and about 350 microns). The pore size can also be selected to remove larger fecal debris and thus help clarify the sample and thus reduce the possibility of clogging filters at subsequent steps in the method.

Filtrate is then placed into a second vessel and passed through a second filtration membrane whose pore size is small enough to retain helminth eggs (e.g., between about 20 microns and about 45 microns), but allow the passage and removal of smaller particles, including yeast and fungal cells.

In another embodiment of the invention, sample is passed through multiple filters or sequentially reducing pore size in order to gradually remove larger particles while retaining eggs before reaching the final filter that retains the eggs.

Upon capture of eggs by the filter, an egg binding/detection reagent is added to bind to the eggs. The binding regent can comprise, but is not limited to, a GlcNac binding protein (e.g., an antibody, a lectin, or CBD. The detection reagent can comprise, but is not limited to an enzyme, a chromophore, a fluorophores, colored micro- or nanospheres, quantum dots or colloidal metals. The binding reagent may be directly chemically coupled to the capture reagent to form a single molecular entity (for example chemical coupling of an egg specific antibody or CBD to an enzyme such as horse radish peroxidase using protein cross-linking chemistries well known in the art), or may be associated with by non-covalent (for example electrostatic or hydrophobic) interactions. In one embodiment of the invention, the binding reagent includes a His6 tag and the detection reagent contains an attached metal such as nickel, copper or cobalt to facilitate the interaction. If the binding and detection reagents are not covalently attached, then they be premixed to facilitate their interaction before addition to the egg sample, to may be added separately to allow their interaction to occur in the presence of the eggs.

In the case of enzymatic detection agents, the enzyme can optionally be produced as a genetic fusion of both the binding reagent and the enzyme to form a single molecular entity. Once non limiting example would be the fusion of CBD with an alkaline phosphatase gene to produce a CBD-AP fusion protein that could bind to, and be used to detect, eggs. In such instances constructs can be made encoding multiple binding domains (including repeats of the same domain or multiple different domains) and multiple enzyme domains (including repeats of the same domain or multiple different domains), in order to modulate the binding affinities and detection sensitivities of the reagent.

Upon incubation with detection reagent, the sample is filtered again in order to remove unbound reagent while retaining eggs, and optionally washed to ensure complete removal of the unbound reagent.

The number of eggs can then be quantitated either in situ, or following removal of the egg/reagent mixture from the container. In the case of chromophores, fluorophores and other detection agents that can be directly quantified optically, they may first be eluted from the beads using, by way of non-limiting example, acids, alkalis, chaotropic agents, surfactants or salts before detection. Following such release, the reagents may optionally be separated from the eggs by filtration prior to detection.

In the case of enzymatic detection systems, the colored reaction products that indicate the number of eggs present could be soluble or insoluble. In the case of soluble products, their optical intensity may also be determined in situ in the container, or following removal from the container, or following filtration to remove eggs and any remaining fecal particles. Insoluble products may be detected similarly by measuring the turbidity of the suspension, or may additionally filtered through a membrane whose pore size is sufficiently small to retain the products, followed by optical detection on the surface of the filter.

EXAMPLES

The invention is further described in the following examples, which do not limit the scope of the invention described in the claims.

The general principles outlined above can be used to design a large number of systems for detecting the presence and abundance of parasite eggs and protozoan oocytes in fecal suspensions or environmental samples. For the purposes of illustration there follows a number of non-limiting examples of several egg counting assays that can be produced using these principals. These examples are merely provided for the purposes of illustration of some of the many different modes in which the invention can be practiced and should not be considered as descriptive of the entire invention.

Example 1

The present example investigated whether Pluriselect filters having a pore size of 90 microns and 27 microns (Pluriselect PluriStrainer® Cell Strainer) were suitable for a) filtering away unwanted fecal debris, and b) capturing and possibly concentrating strongyle eggs.

Fecal Egg Counts were first estimated for an equine fecal sample using the McMaster method. Five grams of feces were suspended in 45 ml of flotation medium (37.5% glucose/25% sodium chloride). The suspensions were mixed in the Fill Flotac containers with built-in sieves (approximately 0.5 mm mesh size). Two counting chambers were filled (equaling 1.0 ml of suspension examined). This yields a multiplication factor of 10 eggs per gram (EPG).

Then, 10 ml of flotation medium suspension was filtered through a first filter having a pore size of 90 microns. One counting chamber of the McMaster (0.5 ml) was filled with filtrate and examined for presence of eggs. This represents a multiplication factor of approximately 20 EPG.

The flow-through sample was then passed through a second filter having a pore size of 27 microns. Again, 0.5 ml was examined in the McMaster chamber (multiplication factor of approximately 20 EPG). Material collected on the 27 micron filter was resuspended in 1 ml of flotation medium and loaded into one McMaster chamber (0.5 ml), and counted. The multiplication factor here will be about 2 EPG, if the filtrate is resuspended in exactly 0.5 ml.

TABLE 1

|  | McMaster | 90 micron filtrate | 27 micron filtrate | 27 micron re-Suspension |
| --- | --- | --- | --- | --- |
| Equine Fecal Sample 1 | 59 eggs counted (590 EPG) | 27 eggs recovered (540 EPG) | No eggs recovered | 223 eggs counted in the chamber, representing about 446 EPG*. |

*About 200 µl of suspension was still in the pipette and not loaded into the chamber, so the true egg yield was undoubtedly higher - possibly above 600 EPG.

Example 2

Five grams of feces were suspended in 45 ml flotation medium to form a fecal solution. The suspensions were mixed in the Fill Flotac containers with built-in sieves (approximately 0.5 mm mesh size). 10 ml of fecal solution was filtered through a first filter having a pore size of 90 microns (Pluriselect PluriStrainer® Cell Strainer). The flow-through sample was then passed through a second filter having a pore size of 27 microns (Pluriselect PluriStrainer® Cell Strainer) for capture of on the 27 micron filter. The material was bleached (1% hypochlorite solution) on the surface of the 27µ filter and then recovered. Images were captured for unbleached samples and samples bleached for 4, 6 and 8 minutes. FIGS. 3A to 3D are photographs showing samples before and after bleaching (panel A=unbleached; panel B=sample following bleaching for 4 minutes; panel C=sample following bleaching for 6 minutes; and panel D=sample following bleaching for 8 minutes). In the first panel (panel A) the normal unbleached eggs appear as dark oval objects. In the latter panels (panels B-D) the bleached eggs appear translucent. The other dramatic and unexpected effect is the dramatic reduction debris, presumably due to cellulose oxidation, which further facilitates optical measurements.

Example 3

Five grams of feces were suspended in 45 ml of flotation medium to form a fecal solution. The suspensions were mixed in the Fill Flotac containers with built-in sieves (approximately 0.5 mm mesh size). 10 ml of fecal solution was filtered through a first filter having a pore size of 90 microns (Pluriselect PluriStrainer® Cell Strainer). The flow-through sample was then passed through a second filter having a pore size of 27 microns (Pluriselect PluriStrainer® Cell Strainer) for capture of on the 27 micron filter. The material was bleached (1% hypochlorite solution) on the surface of the 27µ filter for 5 minutes. Bleached eggs were then contacted with a reagent solution containing wheat germ agglutinin—FITC (5 mg/ml, Vector Labs) at different dilutions in phosphate buffered saline (PBS) containing a blocking agent (Carboblock, Vector labs)(FIG. 4). WGA incubation time was 15 minutes. Egg suspension was placed under a cover slip and examined by fluorescence microscopy.

Example 4

Figure 6:
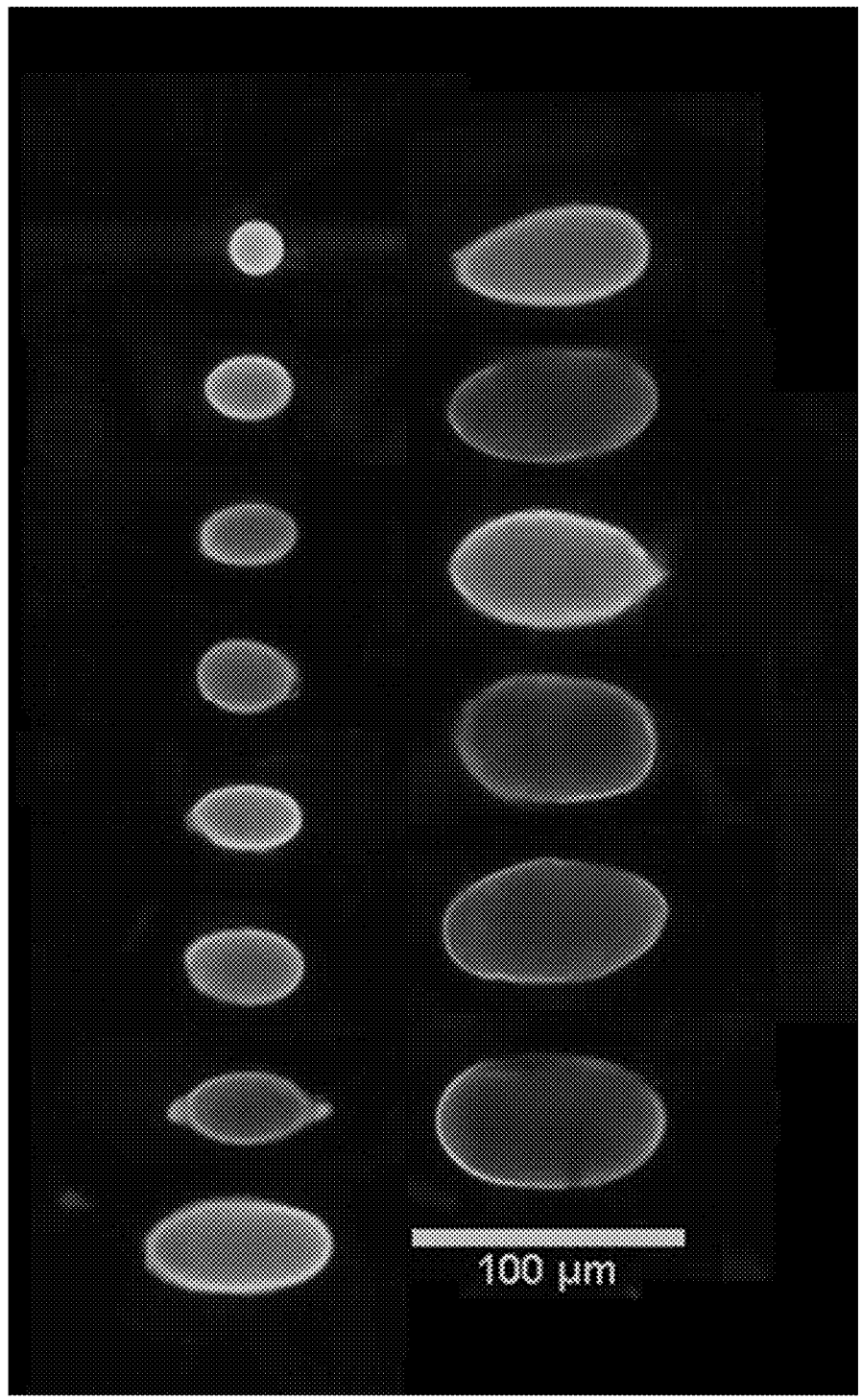
FIG. 6 demonstrates a variety of both helminth eggs and protozoan oocysts from bovine feces stained by CBD conjugated to fluorescein. Bar=200 microns.

CBD was produced by cloning six histidine residues into the pTXB 1 plasmid (New England Biolabs). This produced a fusion protein consisting of an N-terminal His tag followed by the intein endopeptidase and then the CBD of *Bacillus ciruclans* at the C terminus. The protein was expressed cytoplasmically in *E. coli* and purified on a nickel chelate column. The CBD was then labeled using NHS-Fluorescein (Pierce) according to the manufactures instructions (using PBS as the conjugation buffer for 60 minutes at room temperature). After desalting this produced a 6.7 mg/ml CBD solution with between 1.5 and 2 fluorescein molecules per CBD. Feces samples were processed by filtration, bleached and stained with a 1:100 dilution of fluorescent CBD and then imaged on a microscope using phase contrast (FIGS. 5A-E) or fluorescence mode (FIGS. 5F-J). Samples containing strongyles from an adult horse (A,F), ascarids from a foal (B,G) and trichostronglyes from a goat (C, H), a trichostrongyle and a *Trichuris* egg from a cow (D, I) and *Toxocara* eggs from a cat (E, J) are shown. This demonstrates that the CBD from *B. circulans* binds to eggs of several important classes of parasites across numerous diverse species. FIG. 6 shows a montage of various strongyles, a *trichuris* egg and *Coccidia* oocysts from the bovine sample shown in FIG. 5 (D and I). The fact that eggs from such disparate genera were stained demonstrates that chitin serves as a generic marker for multiple helminth parasite eggs and protozoan oocysts. Furthermore, the fact that these eggs and oocyts are clearly stained despite the large amounts of extraneous fecal debris present from the feces demonstrates that, despite its previously reported cross-reaction with cellulose, CBD is clearly capable of discriminating between these fecal components.

Example 5

Figure 7:
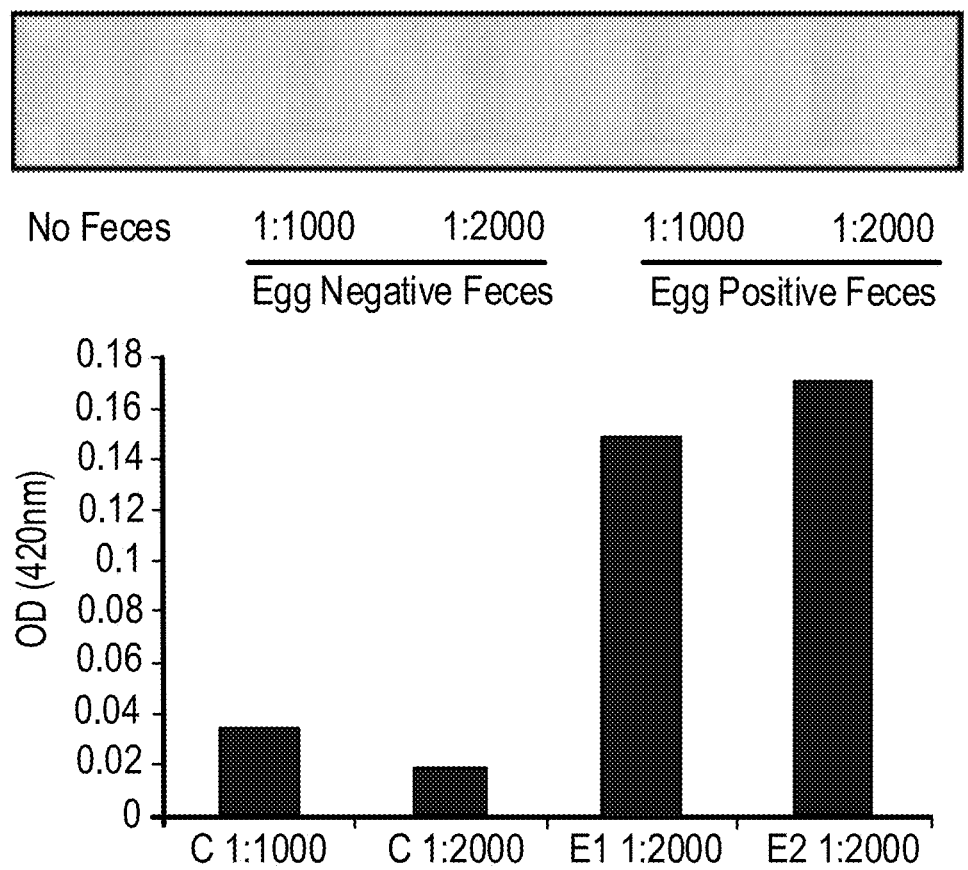
FIG. 7 demonstrates colorimetric detection of eggs in egg positive and egg negative feces.

An equine fecal slurry was passed through a 90 micron filter (Pluriselect PluriStrainer® Cell Strainer) and then entrapped onto a 27 micron filter (Pluriselect PluriStrainer® Cell Strainer) and bleached with 1% hypochlorite for 2 minutes. After washing with PBS the eggs on the filter were contacted with a 1:1000 dilution of 5 mg/ml WGA-biotin conjugate (Vector Labs) in Carboblock/PBS for 15 minutes. The eggs were again washed with PBS and then contacted with a 1:500 dilution of 5 mg/ml streptavidin-alkaline phosphatase conjugate (Vector Labs) in Carboblock/PBS for 15 minutes. After a final wash with PBS, the eggs were contacted with a solution of 5 mM p-nitrophenol phosphase in 100 mM sodium bicarbonate pH 10. After 7 minutes at room temperature samples were photographed and measured with a spectrophotometer, In this was the inventors discriminated between egg positive equine feces (800 eggs/gram) and egg negative feces (FIG. 7). The amount of WGA-AP appeared saturating at both concentrations tested, suggesting that signal-to-noise could be further improved by reducing its concentration.

Example 6

Figure 8A:
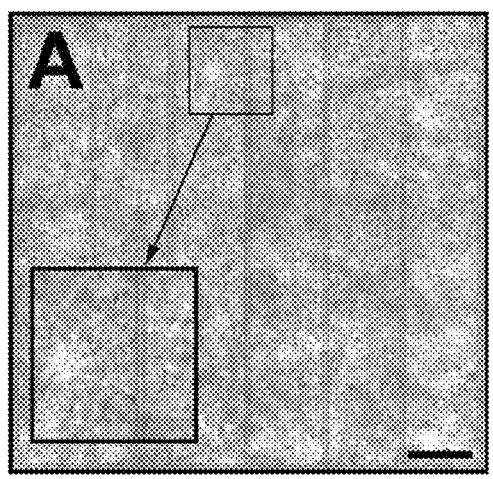
FIGS. 8A and 8B demonstrates imaging of CBD stained eggs from equine feces. A composite image of a McMaster grid was generated at 40× magnification in both phase contrast (A) and fluorescence modes (B). Insets show an enlargement of a representative area including a fungal spore (arrowhead). Bar=1.5 mm.
Figure 8B:
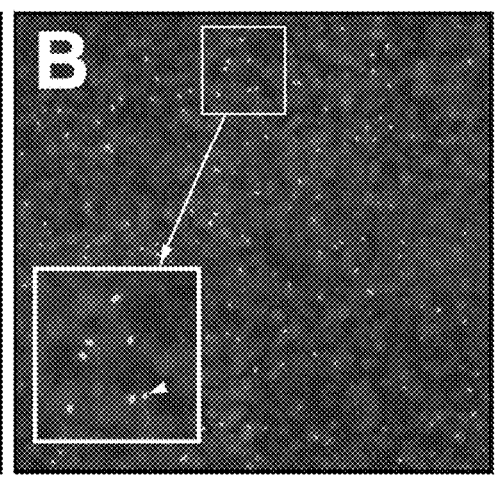

FIGS. 8A and 8B show a composite of 20 images of a McMaster grid of floated, CBD-stained eggs from horse feces taken at 40× on an epifluorescence microscope. Eggs were treated and stained with CBD as described in Example 4. Examination of the sample shows the presence of a small number of fungal spores (FIG. 7B, inset arrowhead) that had not been removed by filtration. Following simple digital processing of the fluorescence image to remove the background (levels and threshold filtering), the inventors were able to quantify the number of eggs by using the particle analysis function of the open source freeware software, Image J, available from the National Institutes of Health. This software allows the user to parse particles by both size and shape, thereby providing a computational method to discriminate between eggs and spores (which are smaller and rounder). Counting by eye led to an egg count of 104 eggs and 19 spores while the Image J software detected 107 eggs and 16 spores. To simulate an image that would be produced by a consumer-grade camera or cell phone, the image was shrunk down from 4800×4800 pixels to 1350× 1350—the equivalent of filling the shorter dimension of an 8 megapixel sensor with the entire McMaster chamber (not just the grid in the image). In this case, the Image J software counted 103 eggs and 20 spores. These data suggest therefore that, in principal, it is possible to couple the chitin-based labelling to this kind of imaging methodology to accurately count eggs within a fecal sample.

The inventors have further shown that such images can be captured with both a consumer-grade camera (Olympus E-PM2 fitted with a macro lens) and a cell phone (Apple iPhone 5s) phone fitted with a macro lens (Olliclip7x) (FIGS. 9A-D). These images were captured with a simple electrophoretic gel fluorescence imaging system (PrepOne Sapphire, EmbiTec) that uses blue LEDs for illumination and an inexpensive orange Perspex plate as an emission filter. These data demonstrate that the construction of an inexpensive imaging system for the visualization of fluorescently stained eggs is possible.

Example 7

Figure 10:
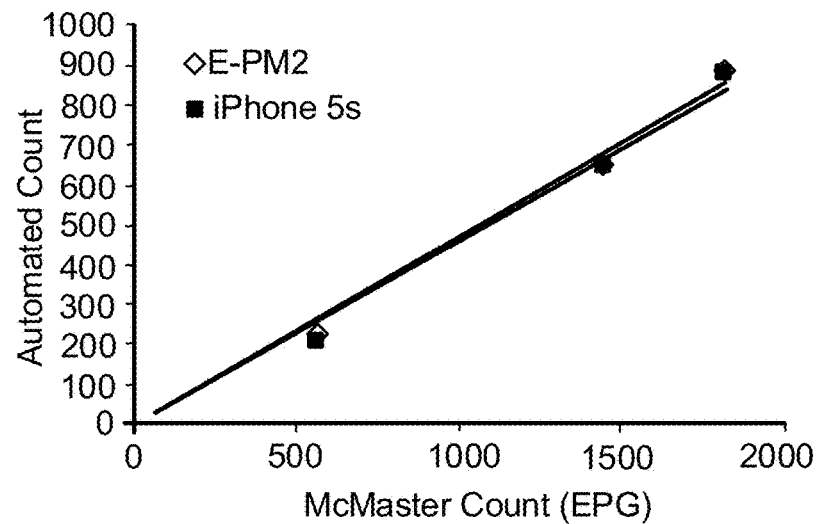
FIG. 10 shows the correlation of traditional McMaster counts with automated counts imaged with both an Olympus consumer grade camera and a cell phone camera. Three fecal samples were evaluated in four independent tests in each case and the results averaged.
Figure 11:
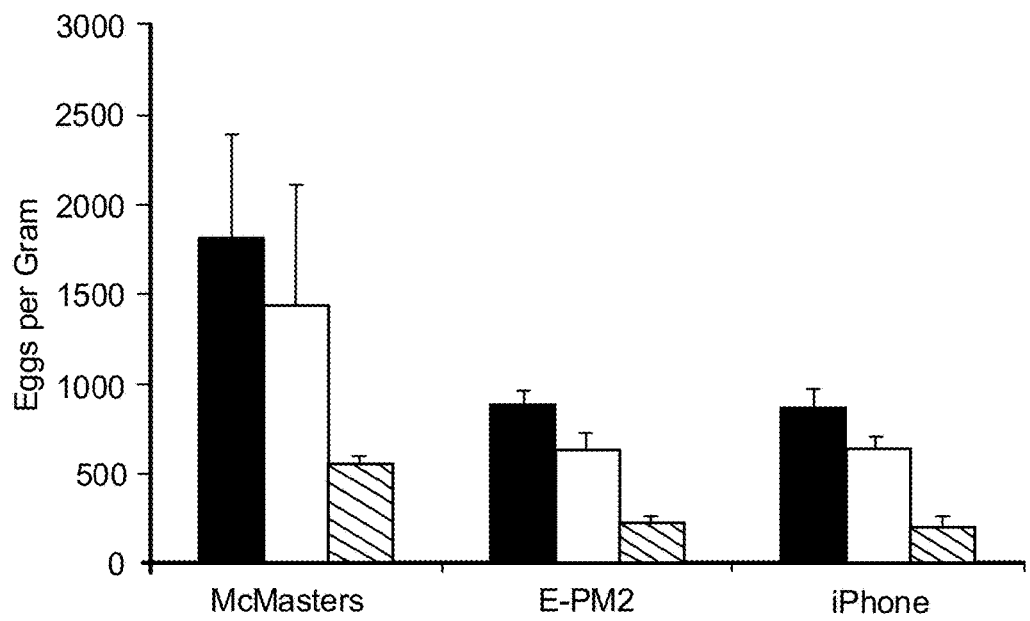
FIG. 11 shows that in general the automated test exhibit less variability than the traditional McMasters method. Average results from FIG. 10 with standard deviations (n=4) are shown.

The inventors have used the above imaging systems to demonstrate that automated egg counts are directly correlated to counts obtained by the standard McMasters methodology. Three equine fecal samples were quantified by the McMasters method or by the method described in Example 6 (n=4) and imaged with both the Olympus E-PM2 and iPhone 5s. Plotting the McMasters count versus automated counts showed that both cameras performed equally well (FIG. 10) and that automated counts were proportional to traditional egg counting. Furthermore, despite the fact that 50% of the eggs input into the automated assay were lost during processing (slope ~0.5), the fact that ten times more feces was analyzed means that the automated assay is still 5 times more sensitive than a McMasters count. Furthermore, in most cases, the variability of the automated method as assessed by standard deviation was superior to the McMasters (FIG. 11).

In some aspects, the methods provided herein can be implemented using a portable testing apparatus combined with a digital camera or smartphone. A non-limiting example of a test apparatus 100 is shown in FIGS. 12-15. The test apparatus 100 includes a stand 110 that includes an upper surface 120 with a camera holder 122. The stand 110 supports a testing circuit board 134 with a light source 132, a camera chamber 130 including a lens mount with integrated emission filter 140, and a testing cradle 150 with a detection chamber for holding the sample. The elements of test apparatus 100 are arranged such that a camera placed in the camera holder 122 can optically access a sample placed in testing cradle 150 via camera chamber 130 and illuminated by light source 132 for image capture, as described above.

Figure 12:
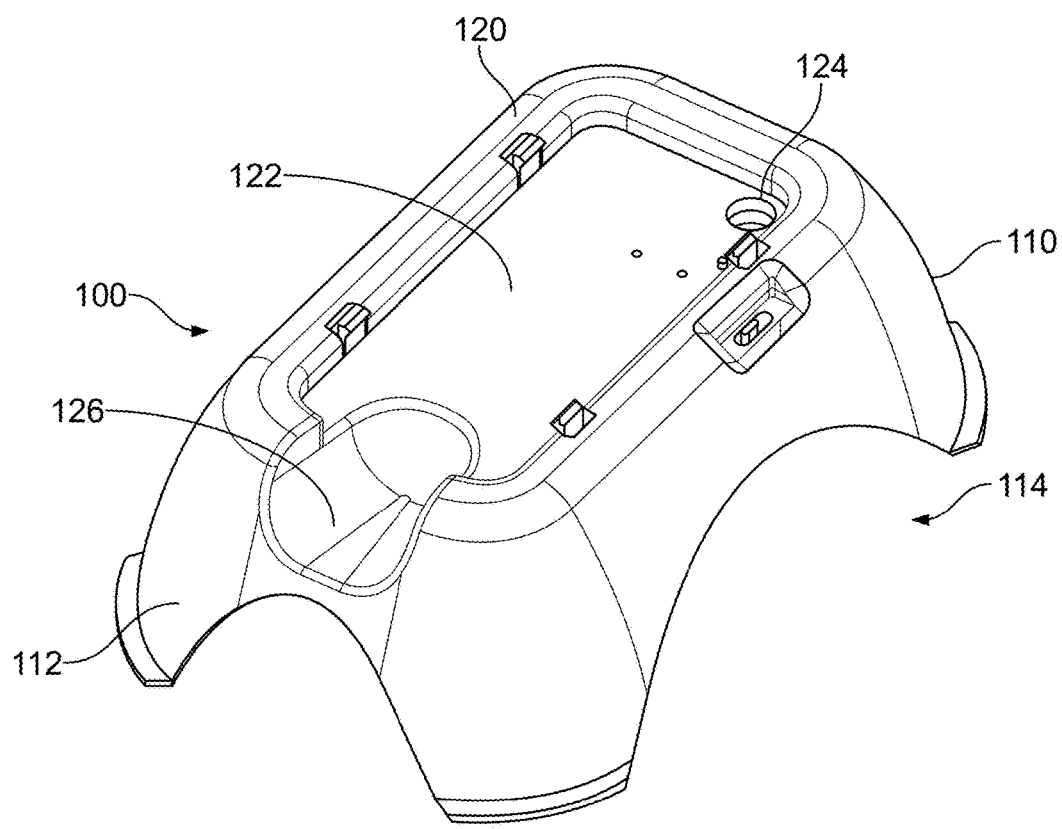
FIG. 12 shows a top isometric view of a testing apparatus for capturing images for samples prepared according to the method described in FIG. 1 or 2.
Figure 14:
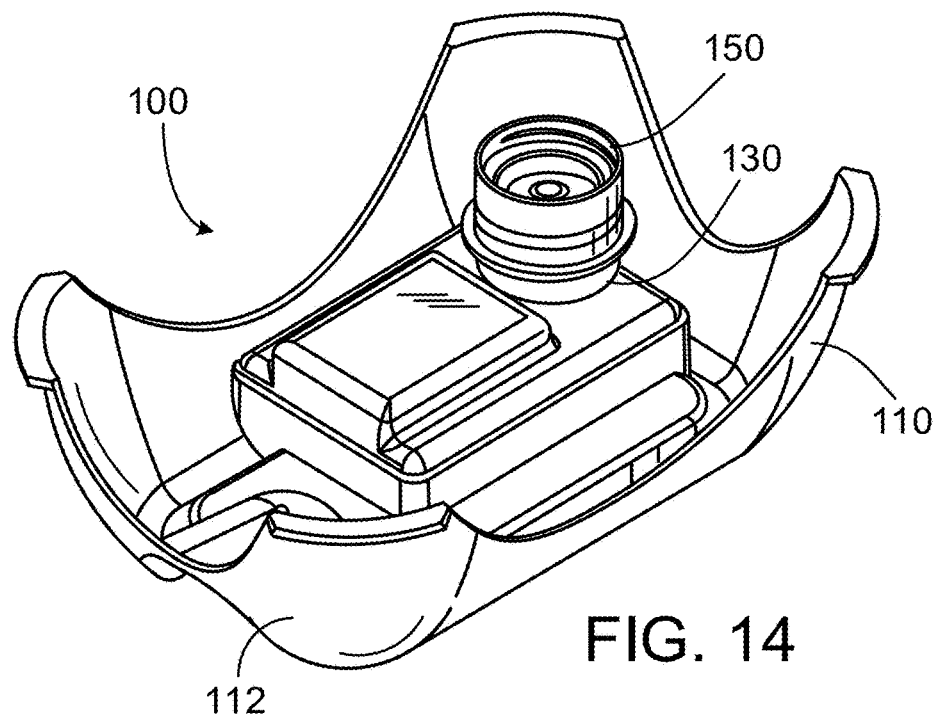
FIG. 14 shows a bottom isometric view of the apparatus of FIG. 12 with an attached sample chamber.
Figure 15:
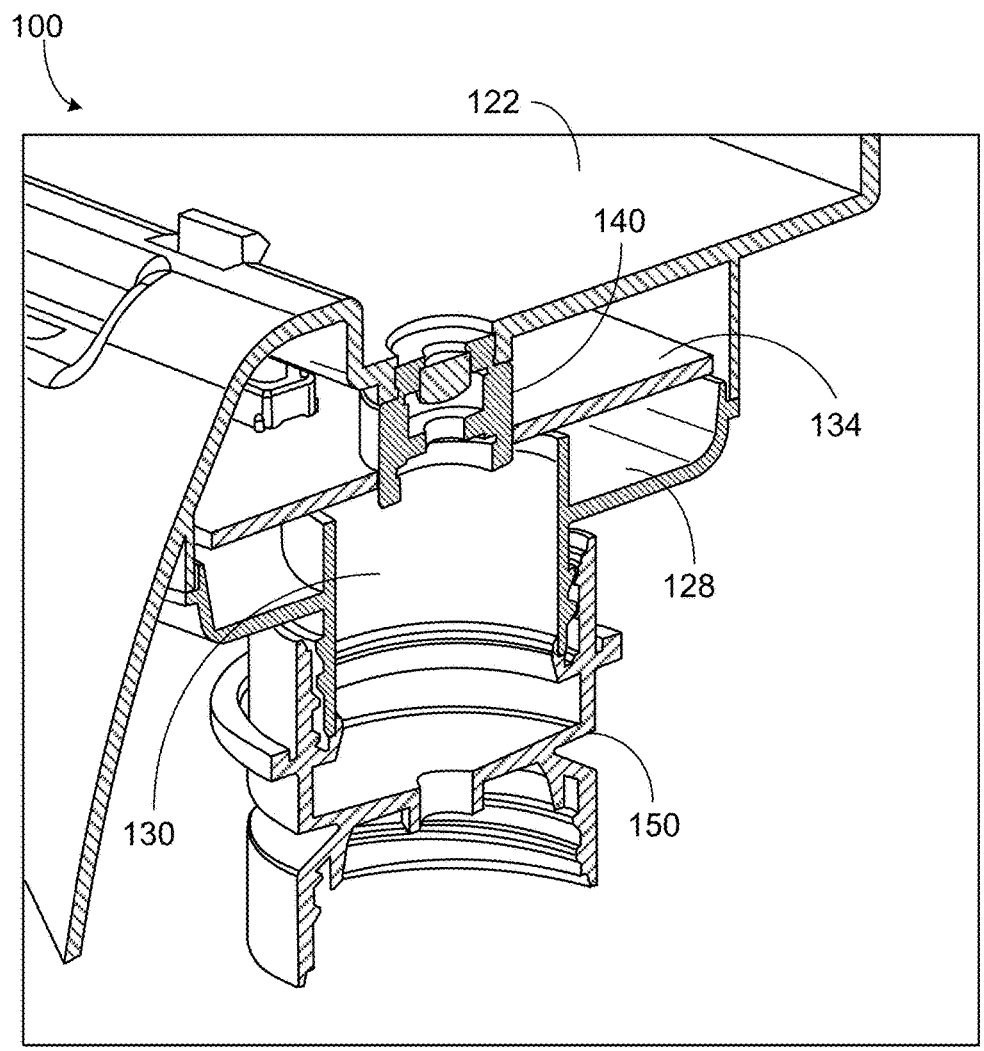
FIG. 15 shows a cross section of a portion of the apparatus and sample chamber shown in FIG. 14.

As shown in FIG. 12, the various elements of test apparatus 100 are attachable to the stand 110. The stand 110 has a generally flat upper surface and four support legs 112. The support legs 112 elevate the upper surface from a table, bench, or other work surface. The support legs 112 are separated by cut-outs 114 that reduce the weight of the stand 110 and allow a user to manipulate the portions of the test apparatus 100 (e.g., the testing cradle 150 as shown in FIGS. 14 and 15) located underneath the upper surface 120.

The upper surface 120 has a large rectangular indentation or blind hole positioned generally in the middle of the upper surface 120, the camera holder 122. The camera holder 122 is configured to retain and align a portable camera such as a digital camera or smartphone with camera capability with the test apparatus 100. The camera holder 122 has an optical access port 124 that permits the camera of the smartphone to detect radiation through the upper surface 120 and from the testing cradle 150 beneath the upper surface 120 (as shown in FIGS. 14 and 15). A user places the smartphone in the camera holder 122 using a grip access 126 located at one end of the upper surface 120.

Figure 13:
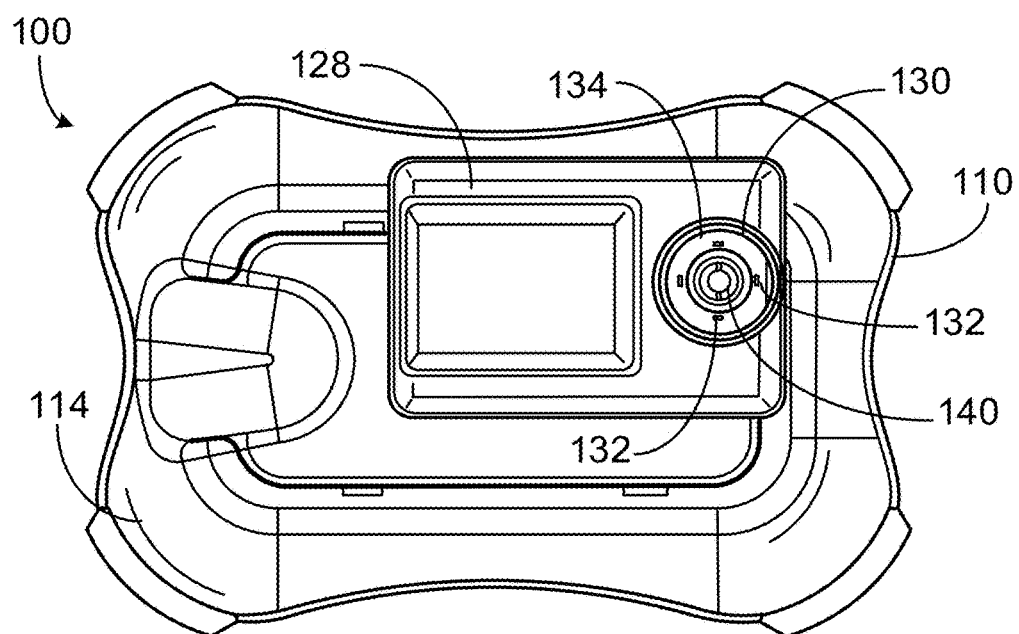
FIG. 13 shows a bottom view of the apparatus of FIG. 12.

Referring to FIG. 13, a bottom view of test apparatus 100 shows the camera chamber 130 affixed to the stand 100. In the bottom view of FIG. 13, the camera chamber 130 appears to surround lens mount 140, the light sources 132, and a portion of a testing circuit 134. Attached to the bottom surface of the stand 100 is a circuit cover 128. As can best be seen in FIG. 15, the circuit cover 128 covers the testing circuit board 134 which is positioned adjacent to the bottom surface of the stand 110. The circuit cover 128 holds the testing circuit board 134 in place and optically aligned with the smartphone above and the testing cradle 150 below the testing circuit board 134. The circuit cover is mounted to the bottom surface of the stand 110 via screw bosses, which align the cover (not shown).

Light sources 132 are located in or on the testing circuit board 134. As described above, light sources 132 can be blue LEDs. The LEDs 132 are arranged on a bottom surface of the testing circuit board 134, such that the LEDs illuminate the camera chamber 130 and the sample in the testing cradle 150 below. Four LEDs 132 are shown in FIG. 12; however, more or fewer LEDs can be used. For example, one, two, or three LEDs can be arranged to surround the lens mount and integrated emission filter 140, or five or more LEDs can be used.

As shown in FIG. 14, a testing cradle 150 is attached to the bottom and testing cradle 150 are threaded so that a testing cradle 150 containing a new sample can be quickly and easily screwed into position on the test apparatus 100. It is also contemplated that camera chamber 130 and testing cradle 150 can be mechanically coupled together via a snap fitting, a quick release mechanism, magnetic coupling, or any other suitable means known in the art that are capable of coupling camera chamber 130 with testing cradle 150. The testing cradle 150 can include one or more filters for separating and attaching the eggs in the sample, as described above. The eggs present in the sample can be bound to one of the filters within testing cradle 150, and optically accessible to the light sources 134 and camera chamber 130.

The fully assembled test apparatus 100 is shown in FIG. 15. Although not shown, a digital camera positioned in camera holder 122 will have unobstructed optical access through the test apparatus 100 via the lens and lens mount 140 attached to the optical access port 124 of the upper surface 120. The light sources 132 (not shown in FIG. 15) on the bottom surface of the testing circuit board 134 illuminate the sample resting below in the in testing cradle 150 and permit acquisition of data such as described above.

In some implementations, the stand 110 is preferably made of lightweight material, e.g., molded or extruded plastic, or lightweight metal such as aluminum. Although the implementation shown in FIGS. 12-14 includes four legs 112 and four cut-outs 114, more or fewer legs and cut-outs are possible. For example, stand 110 may include two wide supporting legs at either end of the upper surface 120 separated by one cut-out on each side of the upper surface 120. Alternatively, the stand 110 can include no legs, and instead be a single solid raised support around the perimeter of upper surface 120, and contain no cut-outs. Other implementations are also possible.

The camera chamber 130 is threaded to allow easy attachment to a testing cradle 150. In some implementations, a chamber cover can be provided, which screws onto the camera chamber 130 and protects the lens and lens mount with integrated emission filter 140 and testing circuit board 134 when a sample and testing cradle 150 is not in place.

In some implementations, the testing circuit board 134 can also support a power source for the light sources 132, e.g., a battery or batteries.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCE LIST (1) Bagley C, Healey M C, Hansen D. Internal Parasites in Cattle. Beef Cattle Handbook. Iowa State University; 2014.
(2) Reinemeyer C R. Controlling Strongyle Parasites of Horses: A Mandate for Change. AAEP Proc 2009; 55:352-360.
(3) Goater T M, Goater C P, Esch G W. Parasitism: The Diversity and Ecology of Animal Parasites. Second ed. Cambridge: Cambridge University Press, 2014.
(4) Stoll N R. On Methods of counting Nematode Ova in Sheep Dung. Parasitology 1930; 22:116-136.
(5) Christie J, Schwan E V, Bodenstein L L, Sommerville J E, van der Merwe L L. The sensitivity of direct faecal examination, direct faecal flotation, modified centrifugal faecal flotation and centrifugal sedimentation/flotation in the diagnosis of canine spirocercosis. J S Afr Vet Assoc 2011; 82:71-75.
(6) James C E, Hudson A L, Davey M W. Drug resistance mechanisms in helminths: is it survival of the fittest? Trends Parasitol 2009; 25:328-335.
(7) Brady H A, Nichols W T. Drug resistance in equine parasites: an emerging global problem. J Equine Vet Sci 2009; 29:285-295.
(8) Nielsen M K, Mittel L, Grice A, Erskine M, Graves E, Vaala W et al. AAEP Parasite Control Guidelines. 2013. American Association of Equine Practioners.
(9) Nicholls J, Obendorf D L. Application of a composite faecal egg count procedure in diagnostic parasitology. Vet Parasitol 1994; 52:337-342.
(10) Rossanigo C E, Gruner L. Accuracy of two methods for counting eggs of sheep nematode parasites. Vet Parasitol 1991; 39:115-121.
(11) Gordon H M, Whitlock H V. A new technique for counting nematode eggs in sheep faeces. J Counc Sci Ind Res 1939; 12:52.
(12) Egwang T G, Slocombe J O. Evaluation of the Cornell-Wisconsin centrifugal flotation technique for recovering trichostrongylid eggs from bovine feces. Can J Comp Med 1982; 46:133-137.
(13) Presland S L, Morgan E R, Coles G C. Counting nematode eggs in equine faecal samples. Vet Rec 2005; 156:208-210.
(14) Cringoli G, Rinaldi L, Veneziano V, Capelli G, Scala A. The influence of flotation solution, sample dilution and the choice of McMaster slide area (volume) on the reliability of the McMaster technique in estimating the faecal egg counts of gastrointestinal strongyles and *Dicrocoelium dendriticum* in sheep. Vet Parasitol 2004; 123: 121-131.
(15) Cringoli G. FLOTAC, a novel apparatus for a multivalent faecal egg count technique. Parassitologia 2006; 48:381-384.
(16) Skotarek S L, Colwell D D, Goater C P. Evaluation of diagnostic techniques for *Anoplocephala perfoliata* in horses from Alberta, Canada. Vet Parasitol 2010; 172: 249-255.
(17) Vadlejch J, Petrtyl M, Zaichenko I et al. Which McMaster egg counting technique is the most reliable? Parasitol Res 2011; 109:1387-1394.
(18) Levecke B, Rinaldi L, Charlier J et al. The bias, accuracy and precision of faecal egg count reduction test results in cattle using McMaster, Cornell-Wisconsin and FLOTAC egg counting methods. Vet Parasitol 2012; 188:194-199.
(19) Egwang T G, Slocombe J O. Efficiency and sensitivity of techniques for recovering nematode eggs from bovine feces. Can J Comp Med 1981; 45:243-248.
(20) Kania S A, Reinemeyer C R. *Anoplocephala perfoliata* coproantigen detection: a preliminary study. Vet Parasitol 2005; 127:115-119.
(21) Andersen U V, Howe D K, Dangoudoubiyam S et al. SvSXP: a *Strongylus vulgaris* antigen with potential for prepatent diagnosis. Parasit Vectors 2013; 6:84.
(22) Nielsen M K, Vidyashankar A N, Gravatte H S, Bellaw J, Lyons E T, Andersen U V. Development of *Strongylus vulgaris*-specific serum antibodies in naturally infected foals. Vet Parasitol 2014; 200:265-270.
(23) Zhang Y, McReynolds L, inventors. Specific detection of chitin using chitin binding domain. patent US 2007/0099234. 2007.
(24) U.S. Pat. No. 5,004,699 to Mark A Winters. Method to detect fungi and yeasts.
(25) Hillrichs K, Schnieder T, Forbes A B, Simcock D C, Pedley K C, Simpson H V. Use of fluorescent lectin binding to distinguish Teladorsagia *circumcincta* and *Haemonchus contortus* eggs, third-stage larvae and adult worms. Parasitol Res 2012; 110:449-458.
(26) Chu, H. H., Hoang, V., Hofemeister, J., and Schrempf, H. (2001). A *Bacillus amyloliquefaciens* ChbB protein binds beta- and alpha-chitin and has homologues in related strains. Microbiology 147, 1793-1803.
(27) Hashimoto, M., Ikegami, T., Seino, S., Ohuchi, N., Fukada, H., Sugiyama, J., Shirakawa, M., and Watanabe, T. (2000). Expression and characterization of the chitin-binding domain of chitinase A1 from *Bacillus circulans* WL-12. J. Bacteriol. 182, 3045-3054.
(28) Montgomery, M. T., Welschmeyer, N. A., and Kirchman, D. L. (1990). A simple assay for chitin: application to sediment trap samples from the subarctic Pacific. Mar. Ecol. Prog. Ser. 64, 301-308.
(29) Reinemeyer, C. R. (2009). Controlling Strongyle Parasites of Horses: A Mandate for Change. AAEP Proc 55, 352-360.
(30) Watanabe, T., Ito, Y., Yamada, T., Hashimoto, M., Sekine, S., and Tanaka, H. (1994). The roles of the C-terminal domain and type III domains of chitinase A1 from *Bacillus circulans* WL-12 in chitin degradation. J. Bacteriol. 176, 4465-4472.
(31) Scott D W and Horn R T (1987) Zoonotic dermatoses of dogs and cats. Vet Clin North Am Small Anim Pract. January; 17(1): 117-44
(32) Steinfeld et al., (2006) (2006). Livestock's Long Shadow. Environmental Issues and Options. (Rome, Italy: FAO).
(33) Piedrafita et al., (2010). Increased production through parasite control: can ancient breeds of sheep teach us new lessons? Trends Parasitol. 26, 568-573.
(34) Perry and Randolph, (1999). Improving the assessment of the economic impact of parasitic diseases and of their control in production animals. Vet. Parasitol. 84, 145-168.
(35) Hoglund et al., (2001). A field survey on the status of internal parasites in calves on organic dairy farms in southwestern Sweden. Vet. Parasitol. 99, 113-128.
(36) Reinhardt et al., (2006). A fenbendazole oral drench in addition to an ivermectin pour-on reduces parasite burden and improves feedlot and carcass performance of finishing heifers compared with endectocides alone. J. Anim Sci. 84, 2243-2250.
(37) Permin et al., (1999). Prevalence of gastrointestinal helminths in different poultry production systems. Br. Poult. Sci. 40, 439-443.
(38) Nansen and Roepstorff, (1987). Resistance of *Oesophagostomum* spp. in pigs to pyrantel citrate. Vet. Parasitol. 24, 229-239.
(39) Duncan, (1985). Internal parasites of the horse and their control. Equine Vet. J. 17, 79-82.
(40) Kaplan R M, (2004). Drug resistance in nematodes of veterinary importance: a status report. Trends Parasitol. 20, 477-481.
(41) da Cruz et al., 2010). Anthelmintic efficacy and management practices in sheep farms from the state of Rio de Janeiro, Brazil. Vet. Parasitol. 170, 340-343.
(43) Cezar et al., (2010). Multiple resistance of gastrointestinal nematodes to nine different drugs in a sheep flock in southern Brazil. Vet. Parasitol. 173, 157-160.
(44) Howell et al., (2008). Prevalence of anthelmintic resistance on sheep and goat farms in the southeastern United States. J. Am. Vet. Med. Assoc. 233, 1913-1919.
(45) Peregrine et al., 2014). Anthelmintic resistance in important parasites of horses: does it really matter? Vet. Parasitol. 201, 1-8.
(46) Gasbarre et al., (2009). Further characterization of a cattle nematode population with demonstrated resistance to current anthelmintics. Vet. Parasitol. 166, 275-280;
(47) Waghorn et al., (2006). Prevalence of anthelmintic resistance on 62 beef cattle farms in the North Island of New Zealand. N. Z. Vet. J. 54, 278-282.
(48) Jackson et al., (2006). Anthelmintic resistance and management of nematode parasites on beef cattle-rearing farms in the North Island of New Zealand. N. Z. Vet. J. 54, 289-296.
(49) Wood et al., (1995). World Association for the Advancement of Veterinary Parasitology (W.A.A.V.P.) second edition of guidelines for evaluating the efficacy of anthelmintics in ruminants (bovine, ovine, caprine). Vet. Parasitol. 58, 181-213.
(50) Vidyashankar et al., (2012). Statistical and biological considerations in evaluating drug efficacy in equine strongyle parasites using fecal egg count data. Vet. Parasitol. 185, 45-56.
(51) Wolstenholme et al., (2004). Drug resistance in veterinary helminths. Trends Parasitol. 20, 469-476.
(52) Sutherland and Leathwick, (2011). Anthelmintic resistance in nematode parasites of cattle: a global issue? Trends Parasitol. 27, 176-181.
(53) Jackson and Coop, (2000). The development of anthelmintic resistance in sheep nematodes. Parasitology 120 Suppl, S95-107.
(54) Roepstorff et al., (1987). Resistance of *Oesophagostomum* spp. in pigs to pyrantel citrate. Vet. Parasitol. 24, 229-239.
(55) Coles et al., (2003). Anthelmintic resistance and use of anthelmintics in horses. Vet. Rec. 153, 636.
(56) Cernanska et al., (2006). A survey on anthelmintic resistance in nematode parasites of sheep in the Slovak Republic. Vet. Parasitol. 135, 39-45.
(57) Kornele et al., (2014). Antiparasitic resistance and grazing livestock in the United States. J. Am. Vet. Med. Assoc. 244, 1020-1022.
(58) Robert et al., (2014). Attitudes towards implementation of surveillance-based parasite control on Kentucky Thoroughbred farms—current strategies, awareness, and willingness-to-pay. Equine Vet. J. In Press.
(59) Demeler et al., (2013). Discrimination of gastrointestinal nematode eggs from crude fecal egg preparations by inhibitor-resistant conventional and real-time PCR. PLoS. One. 8, e61285
(60) Learmount et al., (2009). Development and validation of real-time PCR methods for diagnosis of *Teladorsagia circumcincta* and *Haemonchus contortus* in sheep. Vet. Parasitol. 166, 268-274.
(70) Colditz et al., 2002 Use of lectin binding characteristics to identify gastrointestinal parasite eggs in faeces, Volume 105, Issue 3, 2 May 2002, Pages 219-227.
(71) Palmer and McCombe, (1996). Lectin staining of trichostrongylid nematode eggs of sheep: rapid identification of *Haemonchus contortus* eggs with peanut agglutinin. Int. J. Parasitol. 26, 447-450.
(72) Hillrichs et al., (2012). Use of fluorescent lectin binding to distinguish *Teladorsagia circumcincta* and *Haemonchus contortus* eggs, third-stage larvae and adult worms. Parasitol Res 110, 449-458.
(73) Wharton, (1983). The production and functional morphology of helminth egg-shells. Parasitology 86 (Pt 4), 85-97.
(74) Quiles et al., (2006). In situ characterisation of a microorganism surface by Raman microspectroscopy: the shell of *Ascaris* eggs. Anal. Bioanal. Chem. 386, 249-255.
(75) Coles et al., (2006). The detection of anthelmintic resistance in nematodes of veterinary importance. Vet. Parasitol. 136, 167-185.
(76) Nielsen et al., (2010). Analysis of multiyear studies in horses in Kentucky to ascertain whether counts of eggs and larvae per gram of feces are reliable indicators of numbers of strongyles and ascarids present. Vet. Parasitol. 174, 77-84.
(77) Rudall and Kenchington, (1973). The Chitin System. Biological Rev. 48, 597-633.
(78) Hardt and Laine, (2004). Mutation of active site residues in the chitin-binding domain ChBDChiA1 from chitinase A1 of *Bacillus circulans* alters substrate specificity: use of a green fluorescent protein binding assay. Arch. Biochem. Biophys. 426, 286-297.
(79) Hashimoto et al., (2000). Expression and characterization of the chitin-binding domain of chitinases A1 from *Bacillus circulans* WL-12. J. Bacteriol. 182, 3045-3054.
(80) Gao et al., (2002) Characterisation and developmental expression of a chitinase gene in *Heterodera glycines*. Int. J.Parasitol. 32, 1293-1300.

(81) Arakane et al., (2003). Properties of catalytic, linker and chitin-binding domains of insect chitinase. Insect Biochem. Mol. Biol. 33, 631-648.

(82) Chu et al., (2001). A *Bacillus amyloliquefaciens* ChbB protein binds beta- and alpha-chitin and has homologues in related strains. Microbiology 147, 1793-1803.

(83) Kolbe et al., (1998). The *Streptomyces* reticuli alpha-chitin-binding protein CHB2 and its gene. Microbiology 144 (Pt 5), 1291-1297.

(84) Zeltins and Schrempf, (1995). Visualization of alpha-chitin with a specific chitin-binding protein (CHB1) from *Streptomyces olivaceoviridis*. Anal. Biochem. 231, 287-294.

What is claimed is:

1. A method of detecting the presence or absence of helminth eggs or protozoan oocysts in a fecal sample without the use of a floatation media, the method comprising, sequentially:
    flowing a solution comprising a fecal sample suspended in water or a sample buffer through a first filtration membrane having a pore size of between about 85 microns and about 350 microns to result in a first filtrate, wherein the sample buffer does not have a density greater than the density of a helminth egg or a protozoan oocyst;
    flowing the first filtrate through a second filtration membrane having a pore size of between about 5 microns and about 45 microns to physically capture helminth eggs or protozoan oocysts on the second filtration membrane;
    contacting helminth eggs or protozoan oocysts physically captured on the second filtration membrane with a chitin exposing reagent selected from a surfactant, an oxidizing agent, a chaotrope, an enzyme, and bleach;
    contacting helminth eggs or protozoan oocysts physically captured on the second filtration membrane with a N-acetyl-D-glucosamine binding protein or fragment thereof conjugated to a detectable moiety; and
    imaging the sample captured on the second filtration membrane using an imaging device appropriate for visualizing the detectable moiety to produce an image of particles comprising the detectable moiety;
    electronically parsing the particles in the image by size and shape; and
    detecting the presence or absence of helminth eggs or protozoan oocysts in the fecal sample captured on the second filtration membrane based on the electronic parsing of the particles in the image;
    wherein the imaging device is a portable imaging device, and
    wherein the detection step is performed without suspending helminth eggs or protozoan oocysts captured on the second filtration membrane in water, a sample buffer or floatation media.

2. The method of claim 1, wherein the N-acetyl-D-glucosamine binding protein is selected from the group consisting of a lectin, a chitinase, a chitin binding domain (CBD), or fragments thereof.

3. The method of claim 2, wherein the lectin is selected from the group consisting of wheat germ agglutinin (WGA), soybean agglutinin (SBA), *Maclura pomifera* lectin (MPL), *Bauhinia purpurea* lectin (BPL), *Datura stramonium* lectin (DSL), *Lycopersicon esculentum* lectin (LEL), *Solanum tuberosum* lectin (STL) and *Psophocarpus tetragonolobus* lectin II (PTL-II).

4. The method of claim 1, wherein the detectable moiety is selected from the group consisting of a hapten, an enzyme, an antibody epitope, an antigen, a fluorophore, a radioisotope, a nanoparticle, a member of a binding pair, and a metal chelate.

5. The method of claim 4, wherein the fluorophore is selected from the group consisting of green fluorescent protein, blue fluorescent protein, red fluorescent protein, fluorescein, fluorescein 5-isothiocyanate (FITC), cyanine dye Cy3, cyanine dye Cy3.5, cyanine dye Cy5, cyanine dye Cy5.5, cyanine dye Cy7, dansyl, dansyl chloride (DNS-C1), 5-(iodoacetamida)fluorescein (5-IAF), 6-acryloyl-2-dimethylaminonaphthalene (acrylodan), 7-nitrobenzo-2-oxa-1,3,-diazol-4-yl chloride (NBD-C1), ethidium bromide, Lucifer Yellow, 5 carboxyrhodamine 6G hydrochloride, Lissamine rhodamine B sulfonyl chloride, rhodamine-B-isothiocyanate (RITC), rhodamine 800, tetramethylrhodamine 5-(and 6-)isothiocyanate (TRITC), sulfonyl chloride, 1 anilinonaphthalene-8-sulfonic acid (ANS), 6-(p-toluidinyl)naphthalen-e-2-sulfonic acid (TNS), anthroyl fatty acid, 1,6-diphenyl-1,3,5-hexatriene (DPH), Parinaric acid, 1-(4-trimethylammoniumphenyl)-6-Phenyl-1,3,5-hexatriene p-toluenesulfonate (TMA-DPH), Fluorenyl fatty acid, Fluorescein-phosphatidylethanolamine, Texas red-phosphatidylethanolamine, Pyrenyl-phosphatidylcholine, Fluorenyl-phosphatidylcholine, Merocyanine 540, Naphtyl Styryl, 3,3'dipropylthiadicarbocyanine (diS-C3-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, IR-125, Thiazole Orange, Azure B, Nile Blue, A1 Phthalocyanine, 4', 6-diamidino-2-phenylindole(DAPI), Oxaxine 1, Hoechst 33342, TOTO, Acridine Orange, Ethidium Homodimer, N(ethoxycarbonylmethyl)-6-methoxyquinolinium (MQAE), Fura-2, Calcium Green, Carboxy seminaphtharhodafluorescein-6 (SNARF-6), 1,2-bis(o-aminophenoxy)ethane-N,N,N',N'-tetraacetic acid (BAPTA), coumarin, phytofluors, Coronene, and metal-ligand complexes.

6. The method of claim 1, wherein the portable imaging device is a digital camera, a mobile phone, a smartphone, a tablet, a portable computer, or a scanner.

7. The method of claim 1, wherein the solution comprising a fecal sample is obtained by suspending a fecal sample in water or a sample buffer to form a first fecal solution and flowing the first fecal solution through a bulk filtration membrane having a pore size of between about 400 microns and about 800 microns to obtain the solution comprising the fecal sample.

8. The method of claim 1, further comprising electronically quantifying the number of helminth eggs or protozoan oocysts present in the sample.

9. The method of claim 1, wherein the method is performed without a floatation step to separate the eggs from the fecal material.

10. The method of claim 1, wherein the sample of helminth eggs comprises two or more genera of helminth eggs.

11. The method of claim 10, wherein the two or more genera of helminth eggs are selected from *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Pearsonema, Heterakis, Toxocara, Ascardia, Oxyuris, Unicaria, Toxacaris, Paracaris, Ancylostoma, Necator, Trichinella, Dioctophyme, Eimeria, Coccidia, Bursaphelenchus, Mecistocirrus, Trychostrongylus, Paragonimus, Baylisascaris, Aphelenchoides, Meliodogyne, Heterodera, Globodera, Nacobbus, Pratylenchus, Ditylenchus, Xiphinema, Longidorus, Trichodorus,* and *Enterobius*.

12. The method of claim 10, further comprising quantifying the sample comprising two or more genera of helminth eggs.

13. The method of claim 1, further comprising determining a total fecal egg count in the fecal sample.

14. The method of claim 1, wherein the chitin exposing reagent is bleach.

15. The method of claim 1, wherein the portable imaging device comprises a portable test apparatus having a digital camera or smartphone.

16. The method of claim 15, wherein the test apparatus comprises:
a camera holder;
a light source;
an emission filter; and
a test cradle having a detection chamber for holding the sample.

17. A method of detecting helminth eggs or protozoan oocysts in a fecal sample, without subjecting the fecal sample to a floatation step to separate the eggs from the fecal material, the method comprising, sequentially:
flowing a solution comprising a fecal sample that has not been suspended in a floatation media through a filtration membrane having a pore size of between about 5 microns and about 45 microns to physically capture helminth eggs or protozoan oocysts on a filtration membrane;
contacting helminth eggs or protozoan oocysts physically captured on the filtration membrane with a chitin exposing reagent selected from a surfactant, an oxidizing agent, a chaotrope, an enzyme, and bleach;
contacting helminth eggs or protozoan oocysts physically captured on the filtration membrane with a chitin binding domain (CBD) protein or fragment thereof conjugated to a fluorescein moiety;
imaging the sample captured on the filtration membrane using a portable imaging device appropriate for visualizing the fluorescein moiety to produce an image of particles comprising the fluorescein moiety;
electronically parsing the particles in the image by size and shape; and
detecting the presence or absence of helminth eggs or protozoan oocysts in the fecal sample captured on the filtration membrane based on the electronic parsing of the particles in the image;
wherein the detection step is performed without removing the helminth eggs or protozoan oocysts captured on the filtration membrane.

18. A method of quantifying helminth eggs or protozoan oocysts in a fecal sample, without first subjecting the fecal sample to a floatation step to separate the eggs from the fecal material, the method comprising, sequentially:
flowing a solution comprising a fecal sample that has not been suspended in a floatation media through a filtration membrane having a pore size of between about 5 microns and about 45 microns to physically capture helminth eggs or protozoan oocysts on the filtration membrane;
contacting helminth eggs or protozoan oocysts physically captured on the filtration membrane with a chitin exposing reagent selected from a surfactant, an oxidizing agent, a chaotrope, an enzyme, and bleach;
contacting the helminth eggs or protozoan oocysts captured on the filtration membrane with a chitin binding domain (CBD) protein or fragment thereof conjugated to a fluorescein moiety;
imaging the sample captured on the second filtration membrane using an imaging device appropriate for visualizing the fluorescein moiety to produce an image of particles comprising the fluorescein moiety;
electronically parsing the particles in the image by size and shape; and
quantifying the helminth eggs or protozoan oocysts physically captured on the second filtration membrane based on the electronic parsing of the image,
wherein the imaging device is a portable imaging device, and
wherein the detection step is performed without removing the helminth eggs or protozoan oocysts captured on the filtration membrane.

19. A method of detecting helminth eggs or protozoan oocysts in a fecal sample the method comprising, sequentially:
flowing a solution comprising a fecal sample having a pore size of between about 5 microns and about 45 microns to physically capture helminth eggs or protozoan oocysts on a filtration membrane;
contacting helminth eggs or protozoan oocysts physically captured on the filtration membrane with a chitin exposing reagent selected from a surfactant, an oxidizing agent, a chaotrope, an enzyme, and bleach;
contacting helminth eggs or protozoan oocysts captured on the filtration membrane with a N-acetyl-D-glucosamine binding protein or fragment thereof conjugated to a detectable moiety;
imaging the sample captured on the filtration membrane using a portable imaging device appropriate for visualizing the detectable moiety to produce an image of particles comprising the detectable moiety;
electronically parsing the particles in the image by size and shape; and detecting helminth eggs or protozoan oocysts physically captured on the filtration membrane based on the electronic parsing of the image,
wherein the detection step is performed without removing the helminth eggs or protozoan oocysts captured on the filtration membrane.

20. A method of quantifying helminth eggs or protozoan oocysts in a fecal sample the method comprising, sequentially:
flowing a solution comprising a fecal sample through a filtration membrane having a pore size of between about 5 microns and about 45 microns to physically capture helminth eggs or protozoan oocysts on the filtration membrane;
contacting helminth eggs or protozoan oocysts physically captured on the filtration membrane with a chitin exposing reagent selected from a surfactant, an oxidizing agent, a chaotrope, an enzyme, and bleach;
contacting the helminth eggs or protozoan oocysts physically captured on the filtration membrane with N-acetyl-D-glucosamine binding protein or fragment thereof conjugated to a fluorescein moiety;
imaging the sample captured on the filtration membrane using a portable imaging device appropriate for visualizing the detectable moiety to produce an image of particles comprising the detectable moiety;
electronically parsing the particles in the image by size and shape; and
quantifying the helminth eggs or protozoan oocysts physically captured on the filtration membrane based on the electronic parsing of the image, and wherein the detection step is performed without removing the helminth eggs or protozoan oocysts physically captured on the filtration membrane.

* * * * *

UNITED STATES PATENT AND TRADEMARK OFFICE
CERTIFICATE OF CORRECTION

PATENT NO.        : 9,933,425 B2
APPLICATION NO.   : 14/561780
DATED             : April 3, 2018
INVENTOR(S)       : Pawel Slusarewicz and Eric W. Hauck It is certified that error appears in the above-identified patent and that said Letters Patent is hereby corrected as shown below:

In the Claims

Column 38, Line 13, Claim 5, delete "5 carboxyrhodamine" and insert -- 5-carboxyrhodamine --, therefor.

Column 38, Lines 16-17, Claim 5, delete "1 anilinonaphthalene-8-sulfonic" and insert -- 1-anilinonaphthalene-8-sulfonic --, therefor.

Column 38, Lines 17-18, Claim 5, delete "naphthalen-e-2-sulfonic" and insert -- naphthalene-2-sulfonic --, therefor.

Column 38, Line 24, Claim 5, delete "Naphtyl Styryl," and insert -- Naphthyl Styryl, --, therefor.

Column 38, Line 29, Claim 5, delete "4', 6-diamidino-2-" and insert -- 4',6-diamidino-2- --, therefor.

Column 38, Line 30, Claim 5, delete "Oxaxine" and insert -- Oxazine --, therefor.

Column 38, Lines 61-62, in Claim 11, delete "Unicaria, Toxacaris, Paracaris," and insert -- Uncinaria, Toxascaris and Parascaris --, therefor.

Column 38, Line 64, Claim 11, delete "Trychostrongylus," and insert -- Trichostrongylus, --, therefor.

Column 38, Line 65, Claim 11, delete "Meliodogyne," and insert -- Meloidogyne, --, therefor.

Signed and Sealed this
Tenth Day of July, 2018

Andrei Iancu
*Director of the United States Patent and Trademark Office*